United States Patent
Lee et al.

(10) Patent No.: US 10,631,626 B2
(45) Date of Patent: Apr. 28, 2020

(54) METHOD FOR DETERMINING TOOTH BRUSHING SECTION, AND SMART TOOTHBRUSH AND ELECTRONIC DEVICE THEREFOR

(71) Applicants: Samsung Electronics Co., Ltd., Suwon-si, Gyeonggi-do (KR); Cheil Worldwide Inc., Seoul (KR)

(72) Inventors: Yeon Joo Lee, Seoul (KR); Jong-ho Choi, Suwon-si (KR); Dong-ju Roh, Uiwang-si (KR); Sung-jin Park, Suwon-si (KR); Dong-jun Lee, Ulsan (KR); Jee-yun Lee, Seoul (KR)

(73) Assignees: Samsung Electronics Co., Ltd., Suwon-si (KR); Cheil Worldwide Inc., Seoul (KR)

( * ) Notice: Subject to any disclaimer, the term of this patent is extended or adjusted under 35 U.S.C. 154(b) by 8 days.

(21) Appl. No.: 15/730,169

(22) Filed: Oct. 11, 2017

(65) Prior Publication Data
US 2018/0098620 A1 Apr. 12, 2018

Related U.S. Application Data

(60) Provisional application No. 62/406,533, filed on Oct. 11, 2016.

(30) Foreign Application Priority Data

Jan. 26, 2017 (KR) .................. 10-2017-0012773

(51) Int. Cl.
*A46B 15/00* (2006.01)
*A61B 5/01* (2006.01)
(Continued)

(52) U.S. Cl.
CPC ...... *A46B 15/0004* (2013.01); *A46B 15/0014* (2013.01); *A61B 5/0002* (2013.01);
(Continued)

(58) Field of Classification Search
CPC ............ A46B 15/0004; A46B 15/0014; A61B 5/0008; A61B 5/01; A61B 5/682; A61C 17/221
See application file for complete search history.

(56) References Cited

U.S. PATENT DOCUMENTS 8,175,840 B2   5/2012 Hwang et al.
8,272,091 B2   9/2012 Hwang et al.
(Continued)

FOREIGN PATENT DOCUMENTS

CN   104257434 A   1/2015
CN   104770973 A   7/2015
(Continued)

OTHER PUBLICATIONS

Korean Medical Phrmacy; "Monitoring blood glucose level by saliva measurement, practical use within 5 years"; May 30, 2016; http://www.kmpnews.co.kr/news/articlePrint.html?idxno=20345.
(Continued)

*Primary Examiner* — Randall E Chin
(74) *Attorney, Agent, or Firm* — Jefferson IP Law, LLP

(57) ABSTRACT

A smart toothbrush is provided. The smart toothbrush includes a toothbrush head configured to be provided with bristles, a toothbrush body configured to be connected to the toothbrush head and to be able to be held, a temperature sensor configured to measure a temperature within an oral cavity of a user while the user is brushing teeth using the smart toothbrush, and a processor configured to determine a tooth brushing section in which the user is brushing teeth
(Continued)

within the oral cavity, based on a temperature value measured by the temperature sensor.

18 Claims, 23 Drawing Sheets

(51) Int. Cl.
*A61C 17/34* (2006.01)
*A61C 17/22* (2006.01)
*A61B 5/00* (2006.01)
*G09B 19/00* (2006.01)

(52) U.S. Cl.
CPC .............. *A61B 5/0008* (2013.01); *A61B 5/01* (2013.01); *A61B 5/4833* (2013.01); *A61B 5/682* (2013.01); *A61B 5/6887* (2013.01); *A61C 17/22* (2013.01); *A61C 17/3481* (2013.01); *G09B 19/0084* (2013.01); *A46B 15/004* (2013.01); *A46B 15/0044* (2013.01); *A46B 2200/1066* (2013.01); *A61B 5/742* (2013.01); *A61B 2562/0219* (2013.01); *A61B 2562/04* (2013.01); *A61C 17/221* (2013.01)

(56) References Cited

U.S. PATENT DOCUMENTS

| | | | | |
|---|---|---|---|---|
| 10,064,711 | B1* | 9/2018 | Richter | .................... A41H 1/02 |
| 2009/0092955 | A1 | 4/2009 | Hwang | |
| 2014/0310900 | A1 | 10/2014 | Curry et al. | |
| 2014/0323836 | A1* | 10/2014 | Kusukame | ........... A61B 5/6891 600/344 |
| 2015/0230594 | A1* | 8/2015 | De Vries | ............ A46B 15/0014 15/22.1 |
| 2015/0302770 | A1 | 10/2015 | Meriheinae et al. | |

FOREIGN PATENT DOCUMENTS

| | | |
|---|---|---|
| KR | 10-2009-0090916 A | 8/2009 |
| WO | 0147392 A1 | 7/2001 |
| WO | 2009/107047 A1 | 9/2009 |
| WO | 2011/077282 A1 | 6/2011 |
| WO | 2014-202250 A1 | 12/2014 |

OTHER PUBLICATIONS

Ioana Paringenaru; Mouth Guard Monitors Health Markers, Transmits Information Wirelessly to Smart Phone; UC San Diego News Center; Aug. 31, 2015; http://ucsdnews.ucsd.edu/pressrelease/mouth_guard_monitors_health_markers_transmits_information_wirelessly.

Richard Lewis; "Biochip measures glucose in saliva, not blood"; Brown University; Jan. 20, 2012; https://news.brown.edu/articles/2012/01/plasmonic.

* cited by examiner

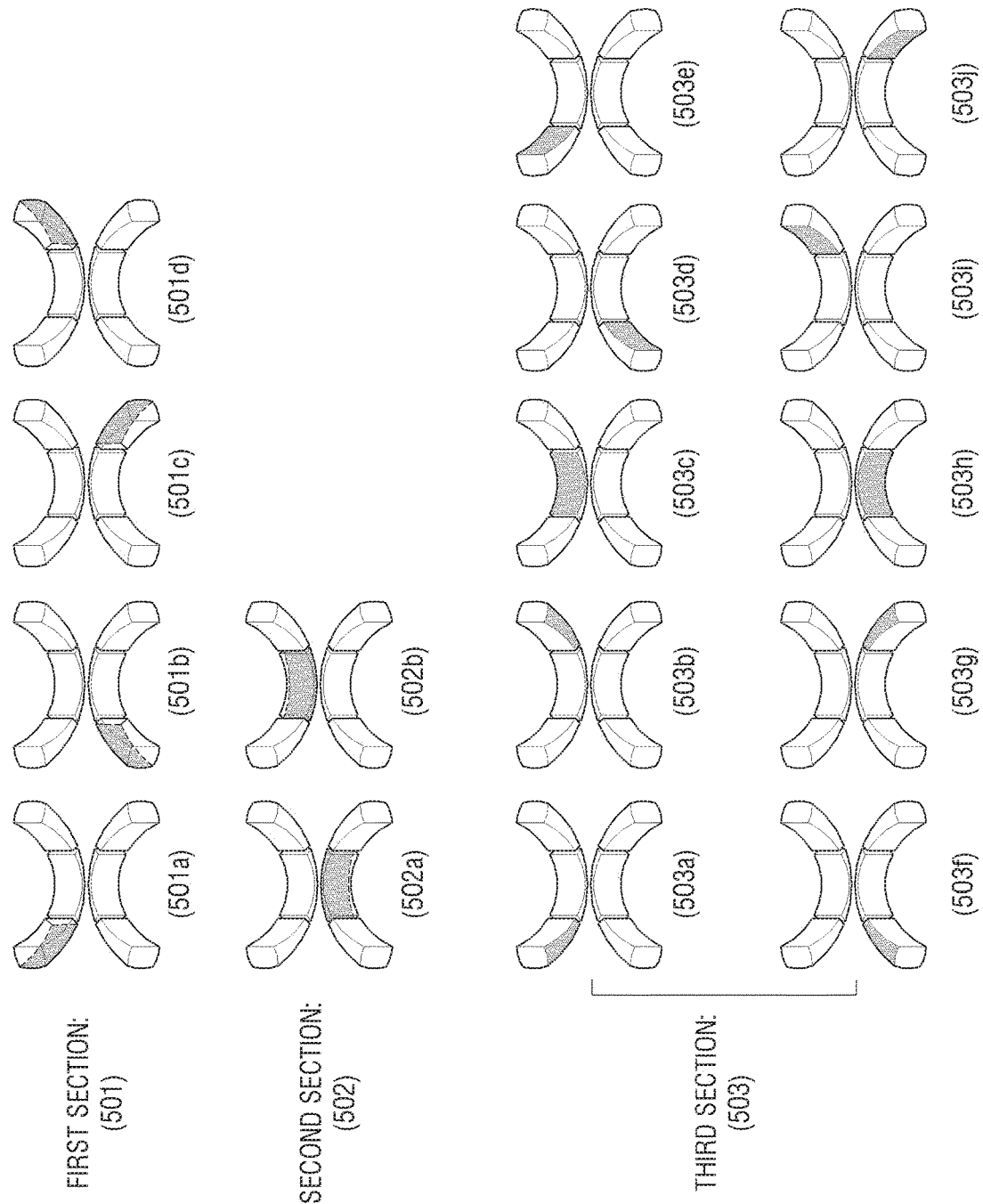

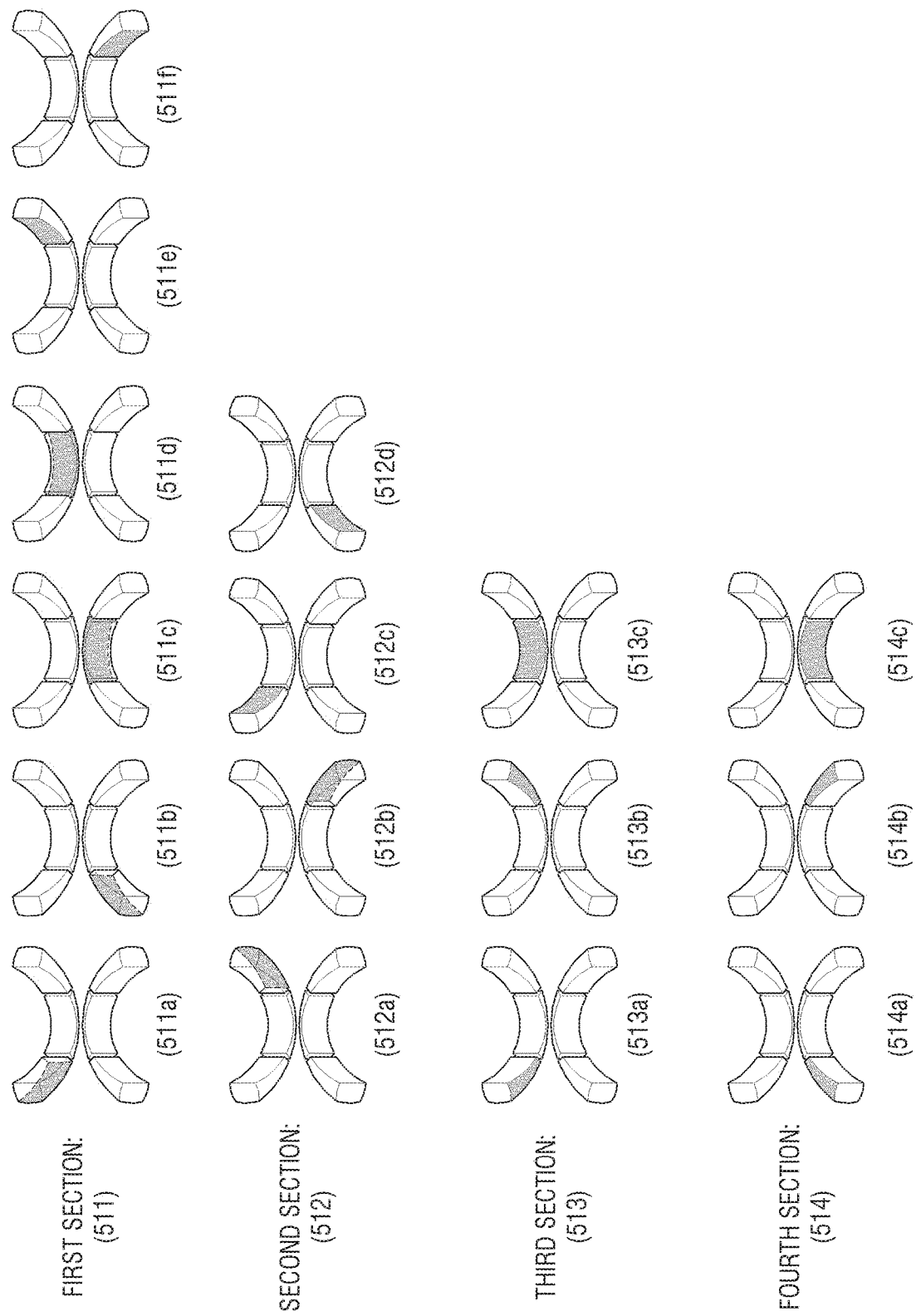

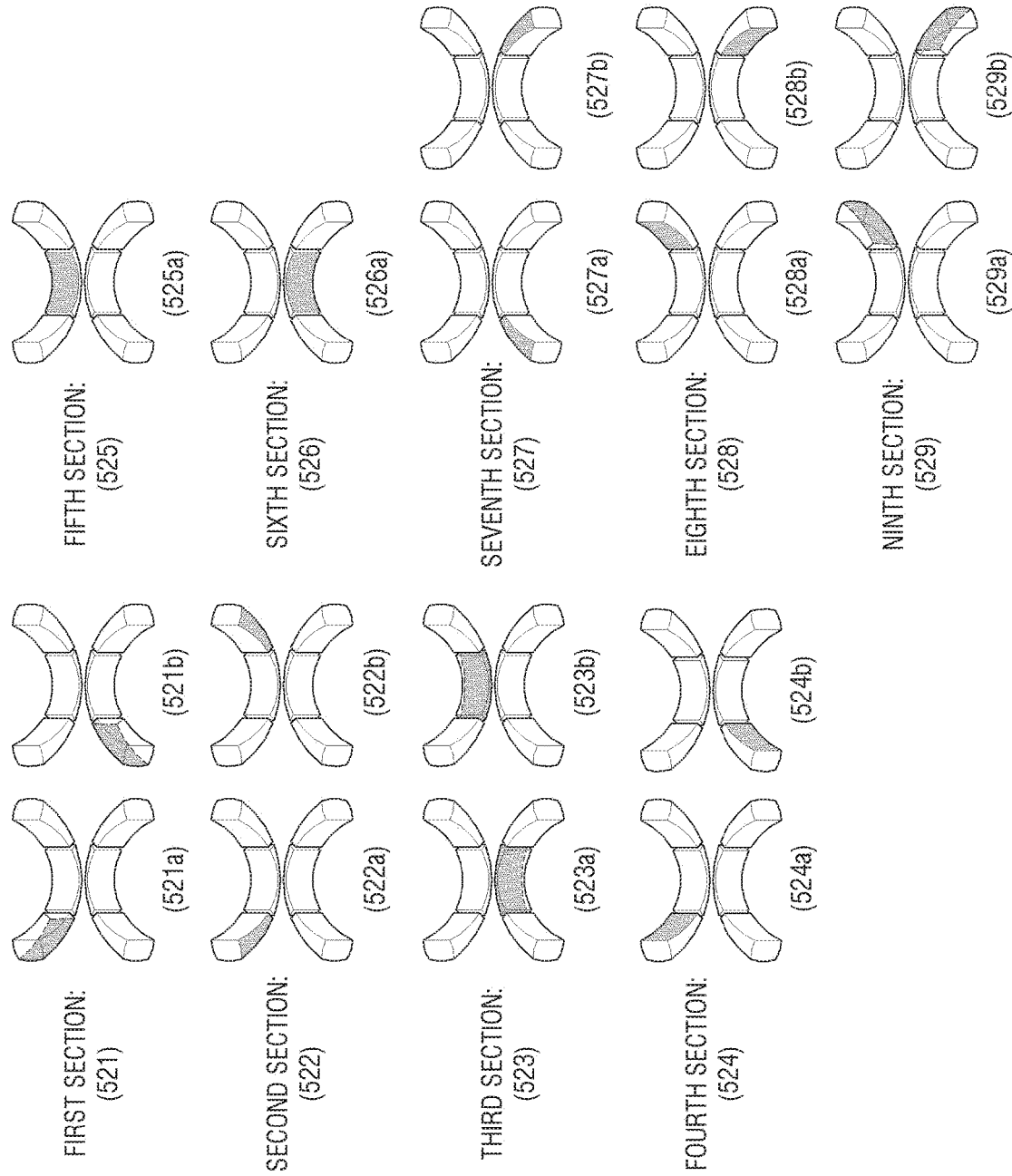

TOOTH BRUSHING AREA

MOTION

TEMPERATURE

<SKIN VICINITY : TEMPERATURE RISING>   <AIR VICINITY : TEMPERATURE FALLING>

FIG. 10A
FIG. 10B
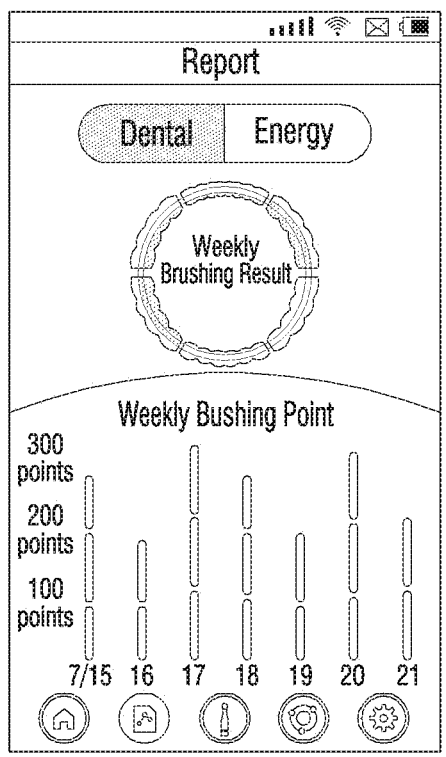
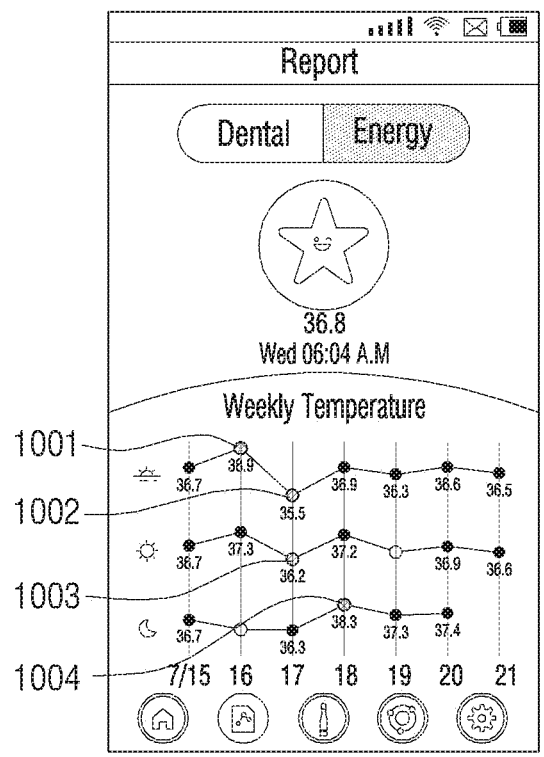

METHOD FOR DETERMINING TOOTH BRUSHING SECTION, AND SMART TOOTHBRUSH AND ELECTRONIC DEVICE THEREFOR

CROSS-REFERENCE TO RELATED APPLICATION(S)

This application claims the benefit under 35 U.S.C. § 119(e) of a U.S. Provisional application filed on Oct. 11, 2016 in the U.S. Patent and Trademark Office and assigned Ser. No. 62/406,533, and under 35 U.S.C. § 119(a) of a Korean patent application filed on Jan. 26, 2017 in the Korean Intellectual Property Office and assigned Serial number 10-2017-0012773, the entire disclosure of each of which is hereby incorporated by reference.

JOINT RESEARCH AGREEMENT

The present disclosure was made by or on behalf of the below listed parties to a joint research agreement. The joint research agreement was in effect on or before the date the present disclosure was made and the present disclosure was made as a result of activities undertaken within the scope of the joint research agreement. The parties to the joint research agreement are 1) Samsung Electronics Co., Ltd., and 2) Cheil Worldwide Inc.

TECHNICAL FIELD

The present disclosure relates to a method for determining a tooth brushing section of a smart toothbrush and a smart toothbrush therefor. More particularly, the present disclosure relates to apparatuses and methods consistent with the present disclosure also relate to a method for determining a tooth brushing section of an electronic device and an electronic device therefor.

BACKGROUND

Tooth brushing means actions of users managing teeth using a manual toothbrush an interdental brush, an electric toothbrush, a sonic toothbrush, a mouthwash, or the like.

In the case of using the manual toothbrush, the user brings cross-sections of bristles of the toothbrush into contact with surfaces of the teeth, and may perform the tooth brushing while performing reciprocation in forward and rearward directions, reciprocation in upward and downward directions, or a rotation motion.

In the case of using the electric toothbrush or the sonic toothbrush, the user may perform the tooth brushing by only an action of brining cross-sections of bristles of the toothbrush into contact with surfaces of the teeth or the vicinity of the surfaces of the teeth.

Correct tooth brushing removes a food residue, dental plaque, or the like, and massages gums to increase a blood supply. In addition, the tooth brushing promotes keratinization of the epithelium of the gums to increase resistance to infection and alleviates halitosis in the oral cavity.

Since the tooth brushing needs to be continuously managed, it is very important to make it a habit to correctly brush teeth since childhood.

Particularly, since teeth of children are weaker than those of adults, in the case in which the teeth of the children are not continuously managed, it is likely that dental caries will be easily generated.

However, it is realistically difficult for parents to continuously manage tooth brushing of their children.

Therefore, a method for naturally forming a tooth brushing habit of a user (for example, a child) and inducing the user to spontaneously brush teeth is required.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a method for determining a tooth brushing section of a smart toothbrush and a smart toothbrush therefor.

In accordance with an aspect of the present disclosure, a smart toothbrush is provided. The smart toothbrush includes a toothbrush head configured to be provided with bristles, a toothbrush body configured to be connected to the toothbrush head and to be able to be held, a temperature sensor configured to measure a temperature within an oral cavity of a user while the user is brushing teeth using the smart toothbrush, and a processor configured to determine a tooth brushing section in which the user is brushing teeth within the oral cavity, based on a temperature value measured by the temperature sensor.

In accordance with another aspect of the present disclosure, an electronic device is provided. The electronic device includes a communicator configured to communicate with a smart toothbrush, and a processor configured to acquire a temperature value within an oral cavity of the user measured by a temperature sensor of the smart toothbrush through the communicator, and determine a tooth brushing section in which the user is brushing teeth within the oral cavity based on the acquired temperature value, while a user is brushing teeth using the smart toothbrush.

In accordance with another aspect of the present disclosure, a method for determining a tooth brushing section of a smart toothbrush is provided. The method includes measuring a temperature within the oral cavity of the user using a temperature sensor of the smart toothbrush while the user is brushing teeth using the smart toothbrush, and determining a tooth brushing section in which the user is brushing teeth within the oral cavity, based on the measured temperature value.

In accordance with another aspect of the present disclosure, a method for determining a tooth brushing section of an electronic device is provided. The method includes acquiring a temperature value within an oral cavity of the user using a temperature sensor of the smart toothbrush while the user is brushing teeth, and determining a tooth brushing section in which the user is brushing teeth within the oral cavity, based on the acquired temperature value.

According to the present disclosure, the user's tooth brushing habits can be formed naturally. For example, the user can perform the correct tooth brushing based on the provision of the accurate tooth brushing guide information or feedback per tooth brushing section, such that the correct habits can be formed.

In addition, the user's bio signal is measured in the non-conscious manner while the user is brushing teeth, such that the health care of the user can be naturally made based on the bio signal.

In addition, it becomes possible for the guardian to monitor and manage the user remotely when the tooth brushing status or the health status of the user (for example, child) is transmitted to the user's guardian (e.g., parent).

Further, the effects that may be obtained or expected by the embodiments of the present disclosure shall be directly or implicitly disclosed in the detailed description of the present disclosure. For example, various effects that may be expected by the various embodiments of the present disclosure shall be disclosed in the detailed description to be described below.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and/or other aspects, features, and advantages of certain embodiments of the present disclosure will be more apparent from the following description taken in conjunction with the accompanying drawings, in which:

FIGS. 5A, 5B, and 5C are views illustrating tooth brushing sections according to various embodiments of the present disclosure;

FIGS. 10A and 10B are screens illustrating historical information according to various embodiments of the present disclosure;

Throughout the drawings, like reference numerals will be understood to refer to like parts, components, and structures.

DETAILED DESCRIPTION

Figure 1A:
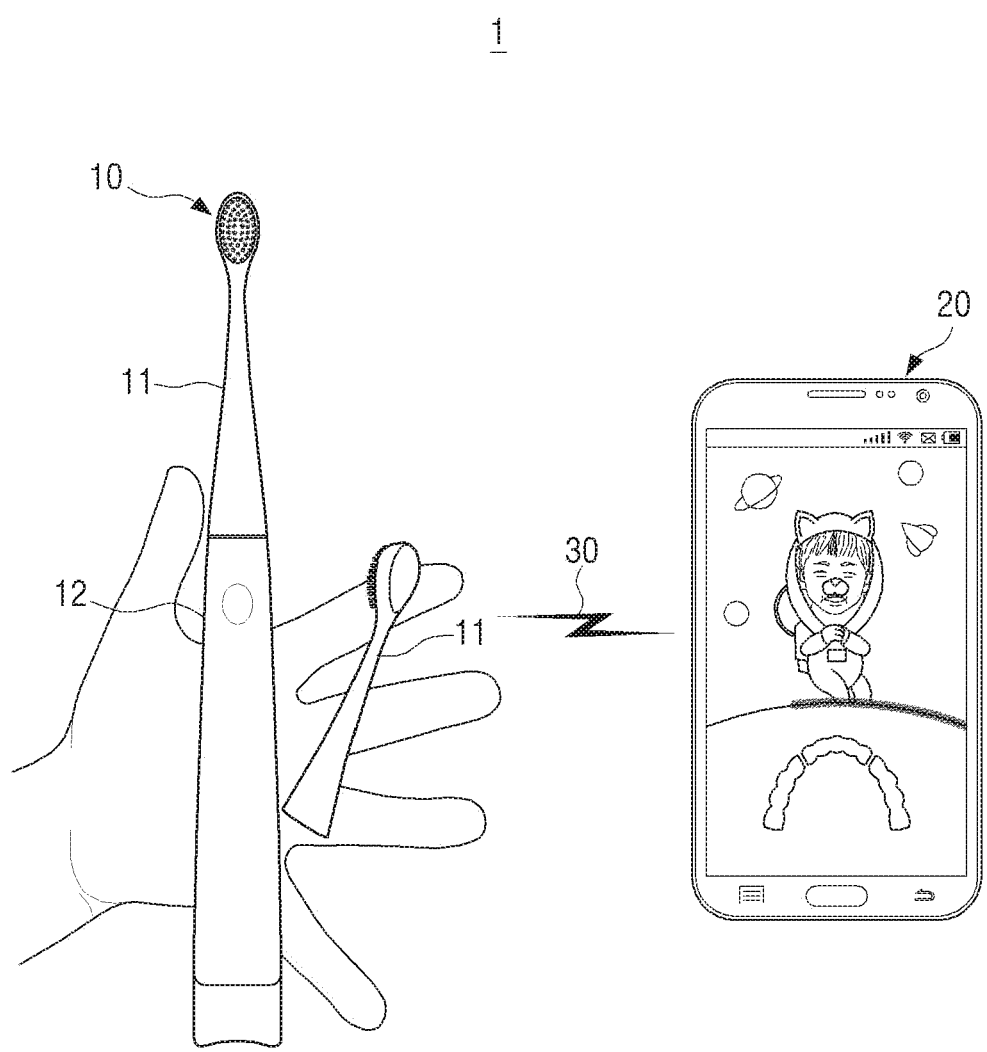
FIGS. 1A, 1B, and 1C are views illustrating a system in which a smart toothbrush and an electronic device are interlocked with each other according to various embodiments of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiment described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

In the present disclosure, an expression "have," "may have," "include," "may include," or the like, indicates existence of a corresponding feature (for example, a numerical value, a function, an operation, a component such as a part, or the like), and does not exclude existence of an additional feature.

In the present disclosure, an expression "A or B," "at least one of A and/or B," "one or more of A and/or B," or the like, may include all possible combinations of items enumerated together. For example, "A or B," "at least one of A and B," or "at least one of A or B" may indicate all of 1) a case in which at least one A is included, 2) a case in which at least one B is included, or 3) a case in which both of at least one A and at least one B are included.

Expressions "first," "second," or the like, used in diverse embodiments may indicate various components regardless of a sequence and/or importance of the components, and do not limit the corresponding components. The abovementioned expressions may be used to distinguish one component from the other component. For example, a first user device and a second user device may indicate different user devices regardless of a sequence or importance thereof. For example, the 'first' component may be named the 'second' component and the 'second' component may also be similarly named the 'first' component, without departing from the scope of the present disclosure.

When it is mentioned that any component (for example, a first component) is (functionally or communicatively) connected to another component (for example, a second component), it is to be understood that any component is directly connected to another component or may be connected to another component through the other component (for example, a third component). On the other hand, when it is mentioned that any component (for example, a first component) is "directly coupled" or "directly connected" to another component (for example, a second component), it is to be understood that the other component (for example, a third component) is not present between any component and another component.

An expression "configured (or set) to" used in the present disclosure may be replaced by an expression "suitable for," "having the capacity to," "designed to," "adapted to," "made to," or "capable of" depending on a situation. A term "configured (or set) to" may not necessarily mean "specifically designed to" in hardware. Instead, an expression "an apparatus configured to" may mean that the apparatus may "do" together with other apparatuses or components. For example, a "processor configured (or set) to perform A, B, and C" may mean a dedicated processor (for example, an embedded processor) for performing the corresponding operations or a generic-purpose processor (for example, a central processing unit (CPU) or an application processor (AP)) that may perform the corresponding operations by executing one or more software programs stored in a memory apparatus.

The electronic device in this disclosure may include, for example, at least one of a smart phone, a tablet personal computer (PC), a mobile phone, a videophone, an electronic book reader, a desktop PC, a laptop PC, a netbook computer, a personal digital assistant (PDA), a portable media player (PMP), an Moving Picture Experts Group (MPEG-1 or MPEG-2) audio layer-3 (MP3) player, a mobile medical instrument, a camera, and a wearable device (e.g., smart glasses, a head wearable device, an electronic apparel, an electronic bracelet, an electronic necklace, an electronic accessory, an electronic tattoo, a smart mirror, or a smart watch).

In some embodiments, the electronic device may be a smart home appliance. The smart home appliances may include, for example, at least one of a television, a digital versatile disc (DVD) player, an audio, a refrigerator, an air conditioner, a vacuum cleaner, an oven, a microwave, a washing machine, an air cleaner, a set top box, a home automation control panel, an electronic dictionary, an electronic key, a camcorder, and an electronic picture frame.

The electronic device according to the embodiment in the present disclosure is also not limited to the above-described devices, and may include new electronic devices according to technological advancement.

Hereinafter, an electronic device according to various embodiments will be described with reference to the accompanying drawings. In the present document, the term user may indicate a person using an electronic device or a device (for example: artificial intelligence electronic device) using an electronic device.

Figure 1B:
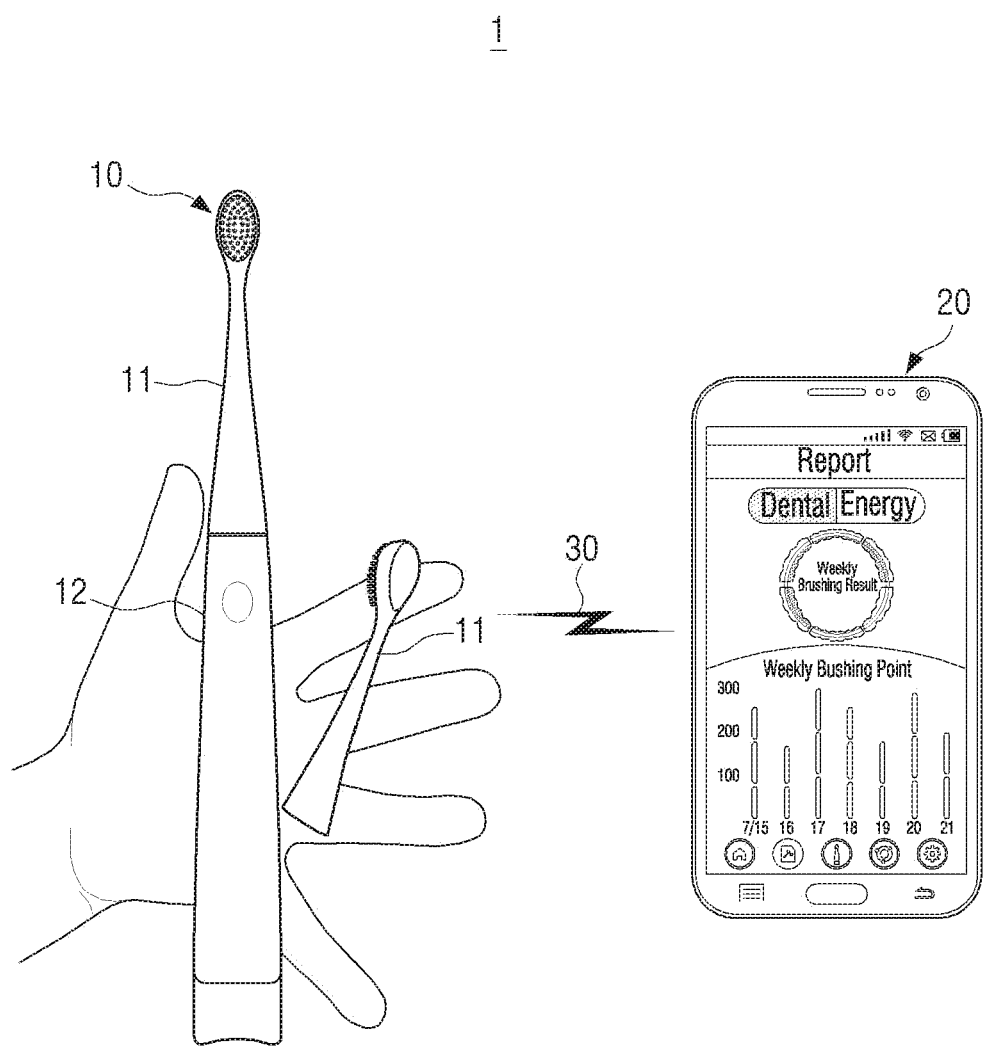
Figure 1C:
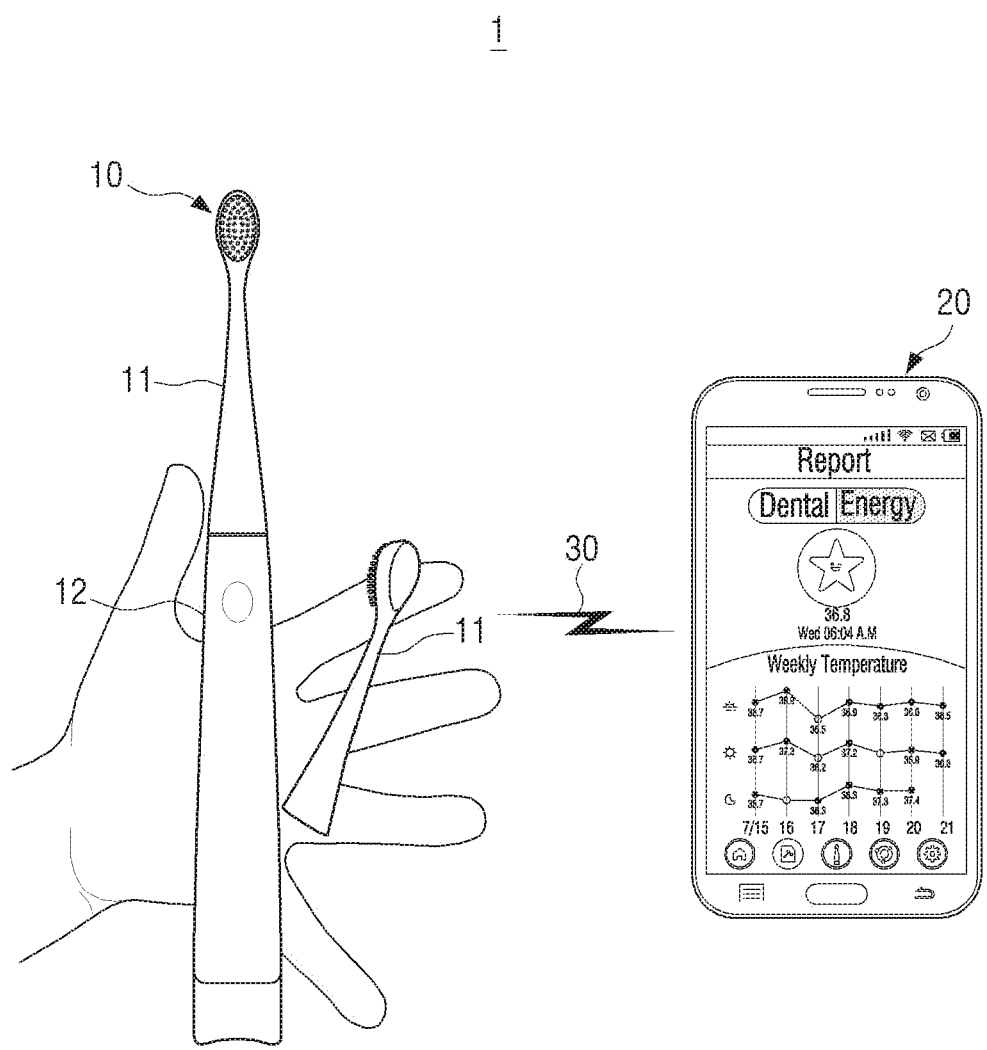

FIGS. 1A, 1B, and 1C are views illustrating a system in which a smart toothbrush and an electronic device are interlocked with each other according to various embodiments of the present disclosure.

Referring to FIGS. 1A, 1B, and 1C, a system 1 may include a smart toothbrush 10 and an electronic device 20 (e.g., a portable terminal).

The smart toothbrush 10 may be a toothbrush capable of providing various additional functions as well as being used as a means for tooth brushing which is an original purpose of a toothbrush.

For example, the smart toothbrush 10 may collect various kinds of sensing values while a user is brushing teeth.

The smart toothbrush 10 may determine a tooth brushing or health condition of a user based on the sensing values collected.

The smart toothbrush 10 may transmit the sensing values to the electronic device 20 which communicates with the smart toothbrush. In this case, the electronic device 20 may use the received sensing values to determine the tooth brushing or health condition of the user.

Further, the smart toothbrush 10 may support a sonic vibration function as a tooth brushing means. For example, the smart toothbrush 10 may provide a sonic vibration effect to assist awkward tooth brushing of a user (e.g., a child).

In an embodiment, the smart toothbrush 10 may measure a temperature within an oral cavity of a user using a temperature sensor provided in the smart toothbrush 10, while the user is brushing teeth.

Based on the measured temperature value, the smart toothbrush 10 may determine a tooth brushing section in which the user is brushing teeth within the oral cavity of the user.

Alternatively, the smart toothbrush 10 may determine a body temperature of a user based on the measured temperature within the oral cavity of the user, without user's self-awareness.

In various embodiments, the smart toothbrush 10 may be configured so that a replaceable toothbrush head may be detached from a toothbrush body for hygiene purposes.

The smart toothbrush 10 may communicate with the electronic device 20 via a network 30.

For example, the smart toothbrush 10 may perform local area communication with the electronic device.

The local area communication may include at least one of, for example, Wi-Fi, Bluetooth (BT), BT low energy (BLE), Zigbee, near field communication (NFC), magnetic secure transmission, radio frequency (RF), and body area network (BAN).

The electronic device 20 communicates with the smart toothbrush 10 and may provide applications for guiding the tooth brushing of the user or for managing the tooth brushing or health condition of the user, or the like.

The application may be provided while being pre-loaded at the time of sale of the electronic device 20, but may be provided in an app type, for example, via an app market (e.g., Android market). In this case, the user of the electronic device 20 may download and install applications from a server providing the app market.

In an embodiment, the electronic device 20 may acquire a temperature value within the oral cavity of the user from the smart toothbrush 10.

Based on the acquired temperature value, the electronic device 20 may determine the tooth brushing section in which the user is brushing teeth within the oral cavity of the user.

Alternatively, the smart toothbrush 10 may determine the body temperature of the user based on the acquired temperature value.

In various embodiments, as illustrated in FIG. 1A, the electronic device 20 may display, on a screen, tooth brushing guide information and tooth brushing analysis information (for example, the tooth brushing time per tooth brushing section, a tooth brushing area in which a user is brushing teeth, tooth brushing status information indicating a tooth brushing degree, etc.) for the tooth brushing of the user by an augmented reality (AR) technique while the user is brushing teeth.

For example, the electronic device 20 may provide a variety of theme backgrounds and masks to suit the user's taste while the tooth brushing time (e.g., 2 to 3 minutes) of the user is continued to induce the user to enjoy brushing teeth. In addition, the electronic device 20 may provide a predetermined reward (e.g., a mobile sticker) or the like to a user if the user successfully performs tooth brushing to induce the user to steadily brush teeth in order to collect stickers, such that the user may be motivated to perform the tooth brushing.

Alternatively, as illustrated in FIG. 1B, the electronic device 20 may provide the user with a tooth brushing analysis result and tooth brushing management information for the user through the screen after the tooth brushing of the user is completed.

Alternatively, as illustrated in FIG. 1C, the electronic device 20 may determine bio information of a user based on the sensing values measured by the smart toothbrush 10. Then, the electronic device 20 may provide the health condition of the user (for example, degree of an attack of fever, degree of low temperature, etc.) through the screen based on the determined bio information.

FIGS. 1A to 1C will be described in detail below.

Figure 2A:
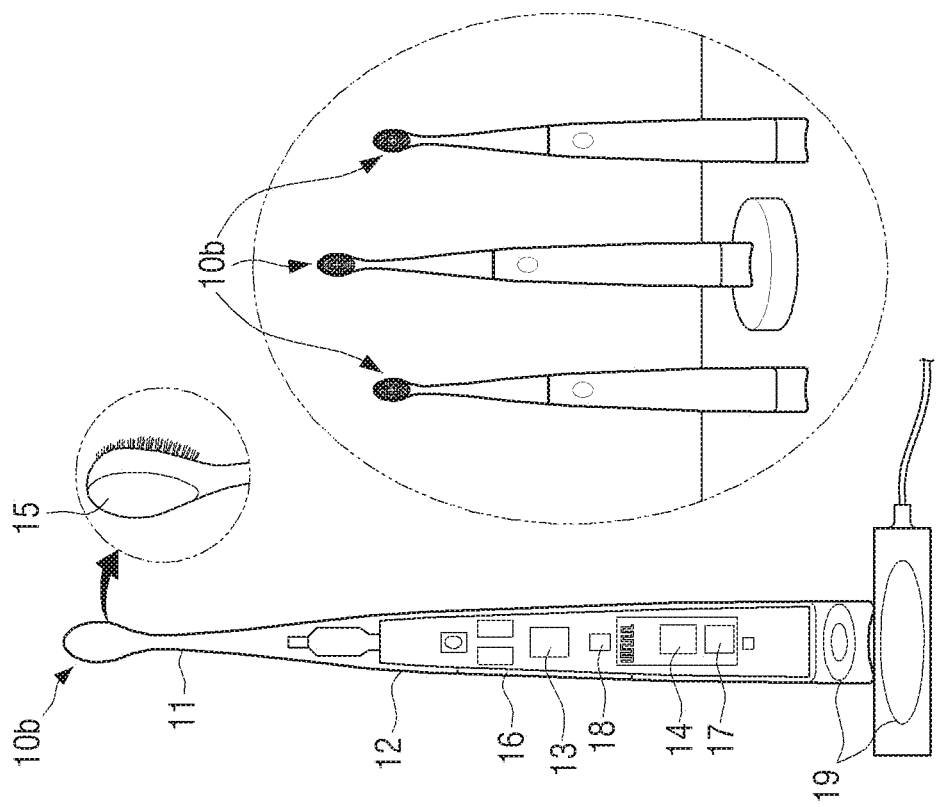
FIGS. 2A and 2B are views illustrating components of a smart toothbrush according to various embodiments of the present disclosure.
Figure 2B:
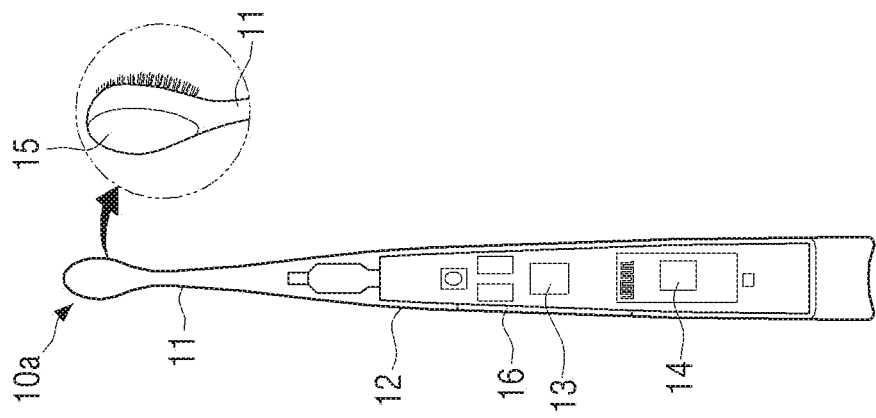

FIGS. 2A and 2B are views illustrating components of a smart toothbrush according to various embodiments of the present disclosure.

Referring to FIGS. 2A and 2B, the smart toothbrush includes a toothbrush head 11, a toothbrush body 12, a processor 13, a memory 14, a temperature sensor 15, and a battery 16, as in a smart toothbrush 10a of FIG. 2A.

The smart toothbrush may have a predetermined length. The predetermined length may be between about 15 cm to about 25 cm as length of a general toothbrush, and may have various lengths depending on a use target (e.g., infant, adult, etc.) of a toothbrush.

The toothbrush head 11 may be connected to the toothbrush body 12 which a user can grip. For example, the toothbrush head 11 may also be injection-molded or formed as an integral part extending up to the toothbrush body 12, or the toothbrush head 11 and the toothbrush body 12 may also have a detachable structure that is separable from or engageable with each other.

The temperature sensor 15 may be provided on the toothbrush head 11 or the toothbrush body 12 and may be preferably provided on the toothbrush head 11.

If the toothbrush head 11 is provided with the temperature sensor 15, the temperature sensor 15 may be provided on a back or side surface of the toothbrush head.

The temperature sensor 15 may comprise, for example, a thermistor located in a cap made of a material (for example, stainless steel, aluminum, etc.) having high conductivity and a low possibility of corrosion. In this case, the thermistor may be fixed to the cap by a highly conductive adhesive (e.g., epoxy or the like). In addition, the cap including the thermistor may also be secured to the toothbrush head 11 or the toothbrush body 12 by the same kind of adhesives as described above.

The processor 13 may be provided on the toothbrush head 11 or the toothbrush body 12, and may be preferably provided on the toothbrush body 12.

The processor 13 may include at least one of a CPU, an AP, and a communication processor (CP). The processor 13 may perform an operation or data processing on a control and/or communication of at least one of the other components of the smart toothbrush 10a.

In various embodiments, the processor 13 may determine a tooth brushing section in which the user is brushing teeth within the oral cavity of the user, based on the temperature value measured by the temperature sensor 15. The tooth brushing section may correspond to at least one of tooth brushing areas which are divided into a tooth surface of a user, a set of a plurality of tooth surfaces, and spaces between teeth.

In various embodiments, the processor 13 may determine the body temperature of the user using the smart toothbrush 10a based on a change rate of the measured temperature value in the body temperature measurement area, if the determined tooth brushing section includes a body temperature measurement area associated with the body temperature measurement of the user.

In various embodiments, the processor 13 may measure the tooth brushing time per tooth brushing section and provide the tooth brushing guide information if the tooth brushing time is equal to or less than a threshold time.

In various embodiments, the processor 13 may determine an operation mode of the smart toothbrush based on a position or a posture of the electronic device around the smart toothbrush.

The memory 14 may include a volatile and/or non-volatile memory. The memory 14 may store, for example, a command or data associated with at least one of the other components of the smart toothbrush 10a. By way of example, the memory 14 may store firmware, software, and/or programs.

In various embodiments, the memory 14 may store an instruction to allow the processor 13 to determine the tooth brushing section in which the user is brushing teeth within the oral cavity of the user, based on the temperature value within the oral cavity of the user measured by the temperature sensor of the smart toothbrush 10a, while the user is brushing teeth using the smart toothbrush.

According to various embodiments, at least one sensor (e.g., a temperature sensor) included in the toothbrush head 11 needs to be wired to be connected to the processor, the memory, or the battery of the toothbrush body 12.

To this end, if the toothbrush head 11 and the toothbrush body 12 are fastened with each other, a structure in which electrodes of the toothbrush head 11 connected from at least one sensor and electrodes of the toothbrush body 12 connected from the processor 13, the memory 14 or the battery 16 meet each other may be considered. For example, there may be a structure in which the toothbrush head 11 and the toothbrush body 12 are fastened with each other by a rotation for strengthening of waterproofing and ease of fastening. In this case, the electrodes of the toothbrush head 11 and the electrodes of the toothbrush body 12 each protrude by a spring so as to make contact points with each other.

According to various embodiments, the smart toothbrush includes the toothbrush head 11, the toothbrush body 12, the processor 13, the memory 14, the temperature sensor 15, the battery 16, a communication unit 17, a motion sensor 18, and a charger 19, as in a smart toothbrush 10b of FIG. 2B.

The toothbrush head 11, the toothbrush body 12, the processor 13, the memory 14, the temperature sensor 15, and the battery 16 of FIG. 2B each correspond to the toothbrush head 11, the toothbrush body 12, the processor 13, the memory 14, the temperature sensor 15, and the battery 16 of FIG. 1B, respectively, and therefore the redundant description thereof will be omitted.

The communication unit 17 may perform wireless communication or wired communication with the electronic device or the server located outside the smart toothbrush.

The wireless communication may include cellular communication using at least one of, for example, long-term evolution (LTE), LTE-advance (LTE-A), code division multiple access (CDMA), wideband CDMA (WCDMA), universal mobile telecommunications system (UNITS), wireless broadband (WiBro), global system for mobile communications (GSM), or the like.

In addition, the wireless communication may include at least one of, for example, Wi-Fi, BT, BLE, ZigBee, NFC, a magnetic secure transmission, an RF, and a BAN.

The wired communication may include at least one of, for example, a universal serial bus (USB), a high definition multimedia interface (HDMI), recommended standard 232 (RS-232), power line communication, plain old telephone service (POTS), or the like.

In various embodiments, the communication unit 17 may also transmit the temperature value measured by the temperature sensor 15 of the smart toothbrush 10b to the electronic device which is communicating with the smart toothbrush 10b.

In various embodiments, the communication unit 17 may also transmit a body temperature value determined based on the change rate of the temperature value to the electronic device which is communicating with the smart toothbrush 10b.

The motion sensor 18 may measure the motion of the smart toothbrush 10b and may include at least one of a gyro sensor, an acceleration sensor, and a geomagnetic sensor. The motion sensor 18 may be provided on the toothbrush head 11 or the toothbrush body 12 of the smart toothbrush 10b, and may be preferably provided on the toothbrush body 12.

For example, the tooth brushing direction of the smart toothbrush 10b may be predicted using the value measured by the acceleration sensor. Alternatively, a rotational angle, a slope, or the like of the smart toothbrush 10b may be predicted using a value measured by a magnetic field sensor. Alternatively, the rotational angle of the smart toothbrush 10b may be corrected using a value measured by the gyro sensor.

The charger 19 may charge the battery 16 using a wired charging technique or a wireless charging technique. For example, this wireless charging technique utilizes wireless power transmission and reception. For example, the battery may be automatically charged by simply placing the smart toothbrush 10b on a charging pad without connecting a separate charging connector. The wireless charging technology may enhance the waterproof function by wirelessly charging the smart toothbrush 10b, and enhance portability since a wired charger is not required. The wireless charging technologies may largely include an electromagnetic induction scheme using a coil, a resonance scheme using resonance, and an RF/microwave radiation which converts electric energy into an electromagnetic wave to transmit power to a long distance.

According to various embodiments, the smart toothbrush 10b may be automatically turned on if separated from the charging pad. In this case, at least one (e.g., a temperature sensor or a motion sensor) of the sensors provided on the smart toothbrush 10b may be turned on together. On the other hand, the smart toothbrush 10b may be automatically turned off if seated on the charging pad.

According to various embodiments, the sensors provided on the smart toothbrush 10b may be turned on stepwise. For example, if the smart toothbrush 10b is separated from the charging pad, the temperature sensor is turned on, and if it is determined based on the temperature value of the temperature sensor that the smart toothbrush 10b has been inserted into the oral cavity, the motion sensor may be turned on.

The processor 13 may determine the tooth brushing section in which the user is brushing teeth within the oral cavity of the user, based on the sensing values measured by the temperature sensor 15 and the motion sensor 18.

In addition, the processor 13 may also determine whether or not the smart toothbrush within the oral cavity of the user touches a skin, a kind of the contacted skin, a status of the contacted skin, or the like, based on the change rate of the temperature value measured by the temperature sensor 15 and the sensing value measured by the motion sensor 18.

Figures 3A, 3B, 3C:
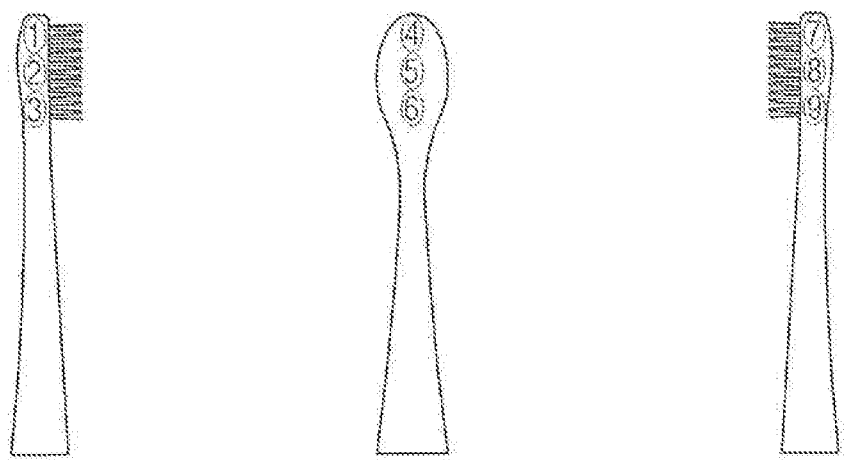
FIGS. 3A, 3B, and 3C are views illustrating a toothbrush head provided with a temperature sensor according to various embodiments of the present disclosure.

FIGS. 3A, 3B, and 3C are views illustrating a toothbrush head provided with a temperature sensor according to various embodiments of the present disclosure.

FIGS. 3A and 3C are side views of the toothbrush head 11 when viewed from a side surface, and FIG. 3B is a rear view of the toothbrush head 11 viewed from a back surface which is an opposite surface of bristles.

Referring to FIGS. 3A, 3B, and 3C, a plurality of temperature sensors may be arranged on a side or back surface of the toothbrush head 11 in an array type.

Meanwhile, FIGS. 3A, 3B, and 3C illustrate that a plurality of temperature sensors are arranged, but one or more temperature sensors may be located at one of the positions of the array type according to the implementation. For example, as illustrated in FIGS. 2A and 2B, one or more temperature sensors may be located in a center (e.g., area 5) of the back surface of the toothbrush head 11.

The smart toothbrush may determine the tooth brushing section in which the user is brushing teeth in the oral cavity of the user based on the temperature value measured by the temperature sensor.

For example, the smart toothbrush may determine whether the place where the smart toothbrush is located is within the oral cavity or outside the oral cavity based on the measured temperature value.

In this case, at least one function of the smart toothbrush may be triggered based on the temperature value measured at the smart toothbrush. For example, if the smart toothbrush is a vibrating toothbrush or a sonic toothbrush, the tooth brushing or cleaning function of the smart toothbrush may be operated.

Alternatively, other sensor functions of the smart toothbrush may be turned on. For example, the motion sensor of the smart toothbrush may be operated. In this case, the tooth brushing section of the smart toothbrush may be more specifically determined based on the measured values of the temperature sensor and the motion sensor. Alternatively, the bio sensor (for example, a temperature sensor, an electrocardiogram sensor, a heart rate sensor, a blood sugar sensor, a body fat measurement sensor, etc.) of the smart toothbrush may be operated. In this case, the bio-signal of the user using the smart toothbrush may be measured, so that the bio information of the user may be determined.

Alternatively, based on the temperature value measured at the smart toothbrush, the operation of the smart toothbrush may be changed.

For example, if it is determined that the place where the smart toothbrush is located is outside the oral cavity based on the measured temperature value, the vibration of the smart toothbrush may be deactivated, a vibration strength may be weakened, or the vibration pattern may be changed.

On the other hand, if it is determined that the place where the smart toothbrush is located is in the oral cavity, the vibration of the smart toothbrush may be activated, the vibration strength may be strengthened, or the vibration pattern may be changed. Alternatively, the vibration strength of the smart toothbrush may be enhanced if the tooth brushing section of the user is a section (for example, molar section) requested to be strongly washed. Alternatively, if the tooth brushing section of the user is a section (for example, a front tooth section) requested to be weakly washed, the vibration strength of the smart toothbrush may be weakened.

According to various embodiments, the temperature sensor may be located on a handle of the toothbrush body for holding the smart toothbrush as well as the toothbrush head of the smart toothbrush.

Also, if the tooth brushing section in which the temperature value is measured is a body temperature measurement area associated with the body temperature measurement of the user, the smart toothbrush or the electronic device communicating with the smart toothbrush may determine the body temperature of the user based on the temperature value measured in the body temperature measurement area. In this case, as the plurality of temperature sensors are arranged in the array type, even if one of the plurality of temperature sensors deviates from the body temperature measurement area, it is possible to continuously and accurately perform the temperature measurement using other temperature sensors.

Also, as the plurality of temperature sensors are arranged in the array type, a location of the smart toothbrush within the oral cavity may be determined. For example, an insertion degree of the smart toothbrush into the oral cavity, whether the smart toothbrush is in contact with the skin, a separation degree of skin, or the like may be determined by using different temperature values measured by the plurality of temperature sensors.

The tooth brushing section determined by the smart toothbrush may be divided into a plurality of sections.

The smart toothbrush may use at least one of a temperature sensor and a motion sensor to determine a tooth brushing section in which the user is brushing teeth.

Alternatively, the electronic device communicating with the smart toothbrush may receive the sensing values measured by the temperature sensor and the motion sensor of the smart toothbrush from the smart toothbrush. The electronic device may determine the tooth brushing section in which the user is brushing teeth based on the received sensing values.

The tooth brushing section may correspond to at least one of a tooth surface of a user, a set of a plurality of tooth surfaces, and tooth brushing areas divided into spaces between teeth. The tooth surface may include at least one of a side surface, a front surface, a back surface, and a top surface of a specific tooth of a user. The set of a plurality of tooth surfaces may include a set of adjacent tooth surfaces. A space between teeth may include a space between two adjacent teeth.

Further, the tooth brushing section determined by the sensing value measured in the smart toothbrush may be a set (or class) of tooth brushing areas including at least one predefined tooth brushing area.

Figure 4:
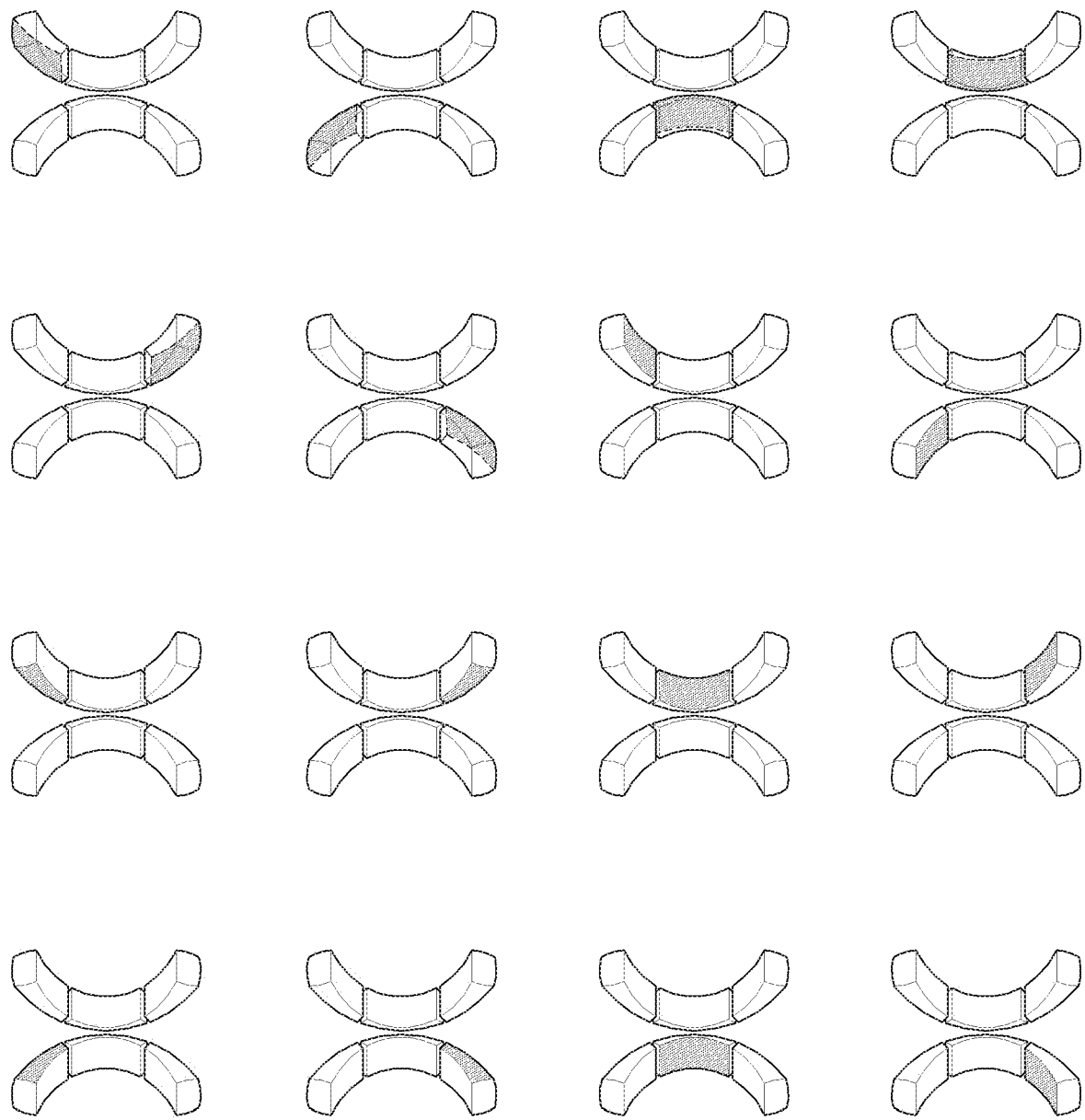
FIG. 4 is views illustrating tooth brushing areas according to an embodiment of the present disclosure.

The tooth brushing areas may be divided into 16 areas according to the location and direction of the teeth, as illustrated in FIG. 4.

FIG. 4 is a view illustrating tooth brushing areas according to an embodiment of the present disclosure.

Referring to FIG. 4, if the molar occlusion surface is not included, the tooth brushing areas may be divided into 12 areas. Alternatively, the tooth brushing areas may also be divided into four areas including maxillary inside, maxillary outside, mandibular inside, and mandibular outside. On the other hand, the divided number of tooth brushing areas is not limited to the above-described number, but the tooth brushing areas may be further subdivided into 16 or more.

If the number of tooth brushing sections is equal to the number of tooth brushing areas, the tooth brushing section may be able to be mapped to the tooth brushing area one to one. On the other hand, the number of tooth brushing sections and the number of tooth brushing areas may be different from each other. For example, if the tooth brushing area is divided into 16 areas, the tooth brushing section may be divided into less than 16 (for example, 4 or 9).

In various embodiments, the tooth brushing section may be determined based on the sensing value in the smart toothbrush, and the finer tooth brushing section may be determined based on other information (e.g., tooth brushing movement section, etc.).

Further, when a plurality of temperature sensors is arranged, the degree of insertion of the smart toothbrush into the oral cavity may be determined depending on the difference in temperature values of the temperature sensors. Accordingly, the tooth brushing section may be determined more finely.

FIGS. 5A, 5B, and 5C illustrate the tooth brushing sections determined in the smart toothbrush according to various embodiments of the present disclosure.

FIG. 5A illustrates the tooth brushing sections that are divided based on the temperature value measured by the temperature sensor of the smart toothbrush.

Referring to FIG. 5A, if there are 16 tooth brushing areas, the tooth brushing sections that are divided based on the temperature value may be divided into a first section 501, a second section 502, and a third section 503.

In this case, if a user brushes tooth brushing areas 501a to 501d, a tooth brushing section of a user may be determined as the first section 501. Further, if a user brushes tooth brushing areas 502a and 502b, the tooth brushing section may be determined as the second section 502. Further, if a user brushes tooth brushing areas 503a to 503j, the tooth brushing section may be determined as the third section 503.

FIG. 5B illustrates the tooth brushing sections that are divided based on the sensing value measured by the motion sensor of the smart toothbrush.

Referring to FIG. 5B, if there are 16 tooth brushing areas, the tooth brushing sections that are divided based on the sensing value may be divided into a first section 511, a second section 512, a third section 513, and a fourth section 514.

In this case, if a user brushes tooth brushing areas 511a to 511f, a tooth brushing section of a user may be determined as the first section 511. Further, if a user brushes tooth brushing areas 512a to 512d, the tooth brushing section may be determined as the second section 512. Further, if a user brushes tooth brushing areas 513a to 513c, the tooth brushing section may be determined as the third section 513. Further, if a user brushes tooth brushing areas 514a to 514c, the tooth brushing section may be determined as the fourth section 514.

FIG. 5C illustrates tooth brushing sections that are divided based on the temperature value measured by the temperature sensor of the smart toothbrush and the sensing value measured by the motion sensor.

Referring to FIG. 5C, if there are 16 tooth brushing areas, tooth brushing sections that are divided based on the temperature value and the sensing value may be divided into a first section 521, a second section 522, a third section 523, a fourth section 524, a fifth section 525, a sixth section 526, a seventh section 527, an eighth section 528, and a ninth section 529.

In this case, if a user brushes tooth brushing areas 521a to 521b, a tooth brushing section of a user may be determined as the first section 521. Further, if a user brushes tooth brushing areas 522a to 522b, the tooth brushing section of the user may be determined as the second section 522. Further, if a user brushes tooth brushing areas 523a to 523b, the tooth brushing section of the user may be determined as the third section 523. Further, if a user brushes tooth brushing areas 524a and 524b, the tooth brushing section of the user may be determined as the fourth section 524. Further, if a user brushes a tooth brushing area 525a, the tooth brushing section of the user may be determined as the fifth section 525. Further, if a user brushes a tooth brushing area 526a, the tooth brushing section of the user may be determined as the sixth section 526. Further, if a user brushes tooth brushing areas 527a and 527b, the tooth brushing section of the user may be determined as the seventh section 527. Further, if a user brushes tooth brushing areas 528a and 528b, the tooth brushing section of the user may be determined as the eighth section 528. Further, if a user brushes tooth brushing areas 529a and 529b, the tooth brushing section of the user may be determined as the ninth section 529.

In an embodiment, the smart toothbrush or the electronic device may use sensors to determine the tooth brushing section in which the user is brushing teeth, as illustrated in FIGS. 5A, 5B, and 5C. The smart toothbrush or the electronic device may provide the tooth brushing guide information based on the result of comparison between the determined tooth brushing sections and the predefined tooth brushing areas.

Specifically, the tooth brushing sections may be more finely divided based on the change rate of the temperature value measured by the temperature sensor of the smart toothbrush.

Figure 6A:
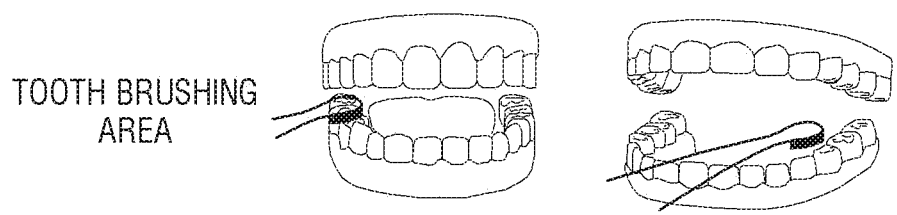
FIGS. 6A, 6B, and 6C are views illustrating processes of determining a tooth brushing section depending on a change rate of a temperature value according to various embodiments of the present disclosure.
Figure 6B:
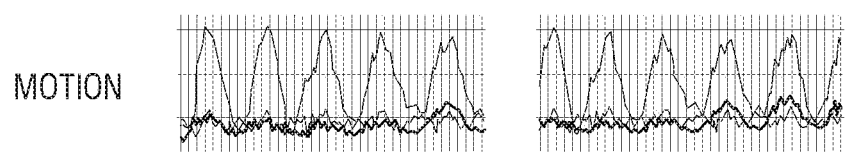
Figure 6C:

FIGS. 6A, 6B, and 6C are views illustrating processes of determining a tooth brushing section depending on a change rate of a temperature value according to various embodiments of the present disclosure.

Referring to FIG. 6A, the user may brush an outside of a right mandible as illustrated in the left drawing, or may brush an inside of a left mandible as illustrated in the right drawing.

The smart toothbrush may measure the sensing value using the sensor of the smart toothbrush while the user is brushing teeth.

FIG. 6B is a view illustrating a sensing value measured by the motion sensor of the smart toothbrush.

Referring to FIG. 6B, the left drawing shows the change rate of the sensing value measured by the motion sensor while the outside of the right mandible is being brushed, and the right drawing shows the change rate of the sensing value measured by the motion sensor while the inside of the left mandible is being brushed.

In this case, the sensing values measured may be almost the same in the left drawing and the right drawing.

That is, the operation of brushing the outside of the right mandible and the operation of brushing the inside of the left mandible by the user are the same, and therefore the motion sensor may hardly distinguish the operations.

Accordingly, the two operations may be distinguished from each other using the temperature value measured by the temperature sensor.

FIG. 6C is a view illustrating the temperature value measured by the motion sensor of the smart toothbrush.

Referring to FIG. 6C, the left drawing shows the change rate of the temperature measured by the temperature sensor while the outside of the right mandible is being brushed, and the right drawing shows the change rate of the temperature measured by the temperature sensor while the inside of the left mandible is being brushed.

In this case, the rates of change of the temperature measured may be different from each other in the left drawing and the right drawing.

That is, as a back side (e.g., an opposite side of the bristles) of a head of the toothbrush provided with the temperature sensor is adjacent to a skin which is a buccal mucosa having a relatively high temperature in the oral cavity while the user is brushing the outside of the right mandible, the temperature may be continued to increase. On the other hand, as the back surface of the head of the toothbrush provided with the temperature sensor does not touch a skin and an inner space of the left mandible is exposed to air or water while the user is brushing the inside of the left mandible, the temperature may be continued to decrease.

Accordingly, if both of the temperature value of the temperature sensor and the sensing value of the motion sensor are used, it is possible to clearly distinguish between the tooth brushing sections in which the user is brushing teeth.

In other words, the tooth brushing area that may not be distinguished only by the sensing value of the motion sensor may be distinguished by using the temperature sensor together.

The smart toothbrush and the electronic device may determine the tooth brushing section in real time, or may determine the tooth brushing section based on the sensing values collected from the beginning to the end of the tooth brushing.

Figure 7A:
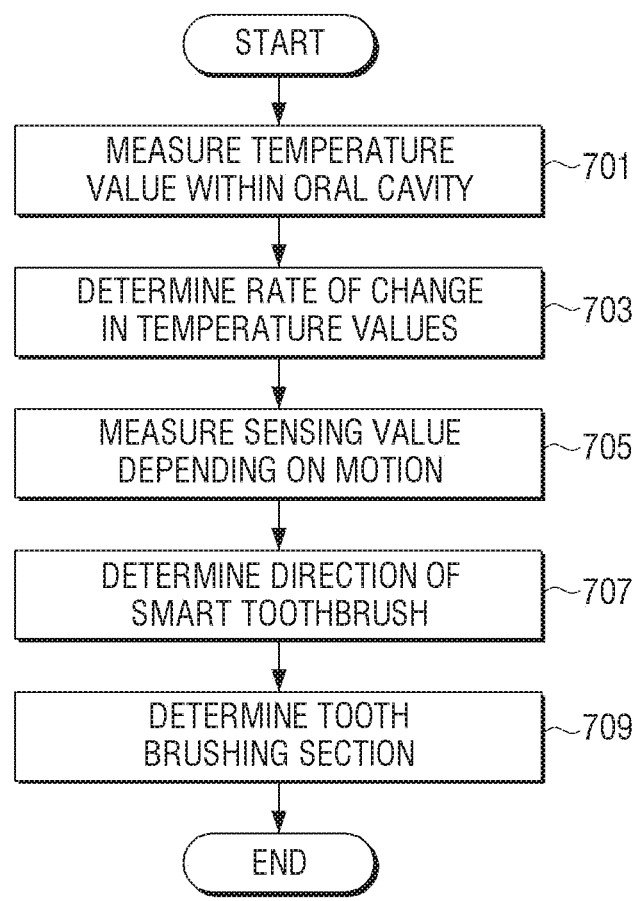
FIGS. 7A and 7B are flow charts illustrating processes of determining a tooth brushing section in which a user is brushing teeth according to various embodiments of the present disclosure.
Figure 7B:
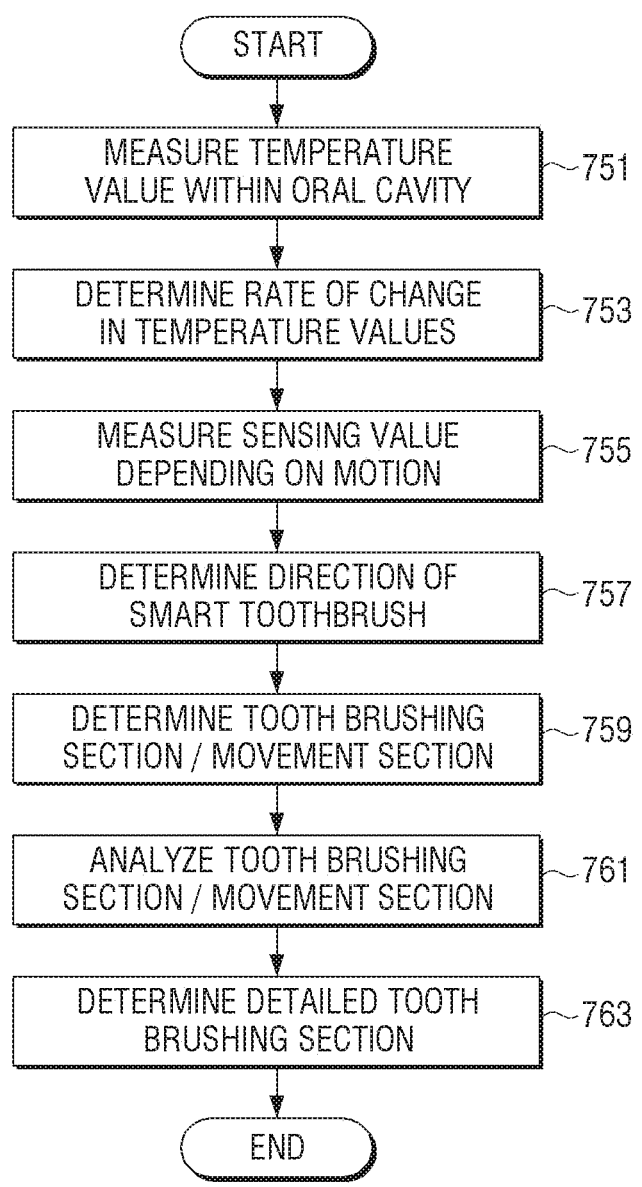

FIGS. 7A and 7B are flow charts in which the user determines the tooth brushing section in which the user is brushing teeth according to various embodiments of the present disclosure.

FIG. 7A is a flow chart for determining a tooth brushing section of a user based on the sensing values collected in real time, and FIG. 7B is a flow chart for determining a tooth brushing section of a user based on the sensing values collected from the beginning to the end of the tooth brushing of the user.

Referring to FIG. 7A, first, in operation 701, the smart toothbrush may measure the temperature values within the oral cavity using a temperature sensor.

Next, in operation 703, the smart toothbrush may determine the rates of change of temperature values based on the measured temperature value.

In addition, in operation 705, the smart toothbrush may use the motion sensor to measure the sensing value depending on the motion of the smart toothbrush.

Next, in operation 707, the smart toothbrush may determine the tooth brushing direction of the smart toothbrush based on the measured sensing value.

In this case, operations 705 and 707 may be performed before operation 701 and operation 703.

Next, in operation 709, the smart toothbrush or the electronic device may determine the tooth brushing section in which the user is brushing teeth. As an example, the smart toothbrush or the electronic device may determine the tooth brushing section based on the temperature value and the sensing value. Alternatively, the smart toothbrush or the electronic device may determine the tooth brushing section based on the rates of change of temperature values and the tooth brushing direction of the smart toothbrush.

The smart toothbrush or the electronic device may compare the tooth brushing section in which the user is brushing teeth with the tooth brushing guide area which is the tooth brushing target area of the user in real time. As an example, the tooth brushing guide area may correspond to the 16 tooth brushing areas of FIG. 4. In this case, the tooth brushing guide area may be changed according to a tooth brushing order and a tooth brushing time. Further, the tooth brushing guide area may be determined according to the oral cavity conditions (e.g., the number of teeth of the user, the size of the teeth, the position of the teeth, etc.) of the user or the treatment history of the user.

Next, the smart toothbrush or the electronic device may provide the tooth brushing guide information according to the comparison result of the tooth brushing area and the guide area.

In various embodiments, the smart toothbrush may determine the tooth brushing section of the user based on the sensing values collected from the beginning to the end of the tooth brushing of the user, as illustrated in FIG. 7B.

Referring to FIG. 7B, first, in operation 751, the smart toothbrush may measure the temperature values within the oral cavity using a temperature sensor.

Next, in operation 753, the smart toothbrush may determine the rates of change of temperature values based on the measured temperature value.

In addition, in operation 755, the smart toothbrush may use the motion sensor to measure the sensing value depending on the motion of the smart toothbrush.

Next, in operation 757, the smart toothbrush may determine the tooth brushing direction of the smart toothbrush based on the measured sensing value.

In this case, operations 755 and 757 may be performed before operation 751 and operation 753.

Next, in operation 759, the smart toothbrush or the electronic device may determine the tooth brushing section of the user in which the tooth brushing is performed from the beginning of the tooth brushing to the end of the tooth brushing, and the movement section of the smart toothbrush in which the tooth brushing is performed. As an example, the smart toothbrush or the electronic device may determine the tooth brushing section and the movement section based on the temperature value and the sensing value. Alternatively, the smart toothbrush or the electronic device may determine the tooth brushing section and the movement section based on the rates of change of temperature values and the tooth brushing direction of the smart toothbrush. In this case, the smart toothbrush may temporarily store sensed values while waiting until the electronic device is connected thereto, and then collectively transmit the sensing values to an external device when the electronic device is connected thereto by a communication manner.

In operation 761, the smart toothbrush or the electronic device may analyze the tooth brushing zone and the movement section of the user. In this case, the electronic device may determine the previous or subsequent tooth brushing section in which the tooth brushing was or will be performed before or after the tooth brushing section per the tooth brushing section.

In operation 763, the smart toothbrush or the electronic device may determine the detailed tooth brushing sections depending on the tooth brushing time of the user based on the analyzed information.

As an example, the detailed tooth brushing sections may correspond to 16 tooth brushing areas of FIGS. 5A, 5B, and 5C.

The smart toothbrush of the present disclosure may be operated in a plurality of modes. By a tentative name, the smart toothbrush may be operated in either a guide mode or a free mode. Generally, the smart toothbrush is operated in the free mode, but the smart toothbrush may be operated in the guide mode under certain circumstances.

For example, the guide mode may refer to a mode in which the external device provides feedback information in real time to guide the tooth brushing of the user based on the sensing value collected from the smart toothbrush.

In addition, the free mode may mean a mode in which the smart toothbrush stores sensing values collected from the beginning to the end of the tooth brushing and provides the tooth brushing analysis result based on the collected sensing values when the tooth brushing ends.

Figure 8:
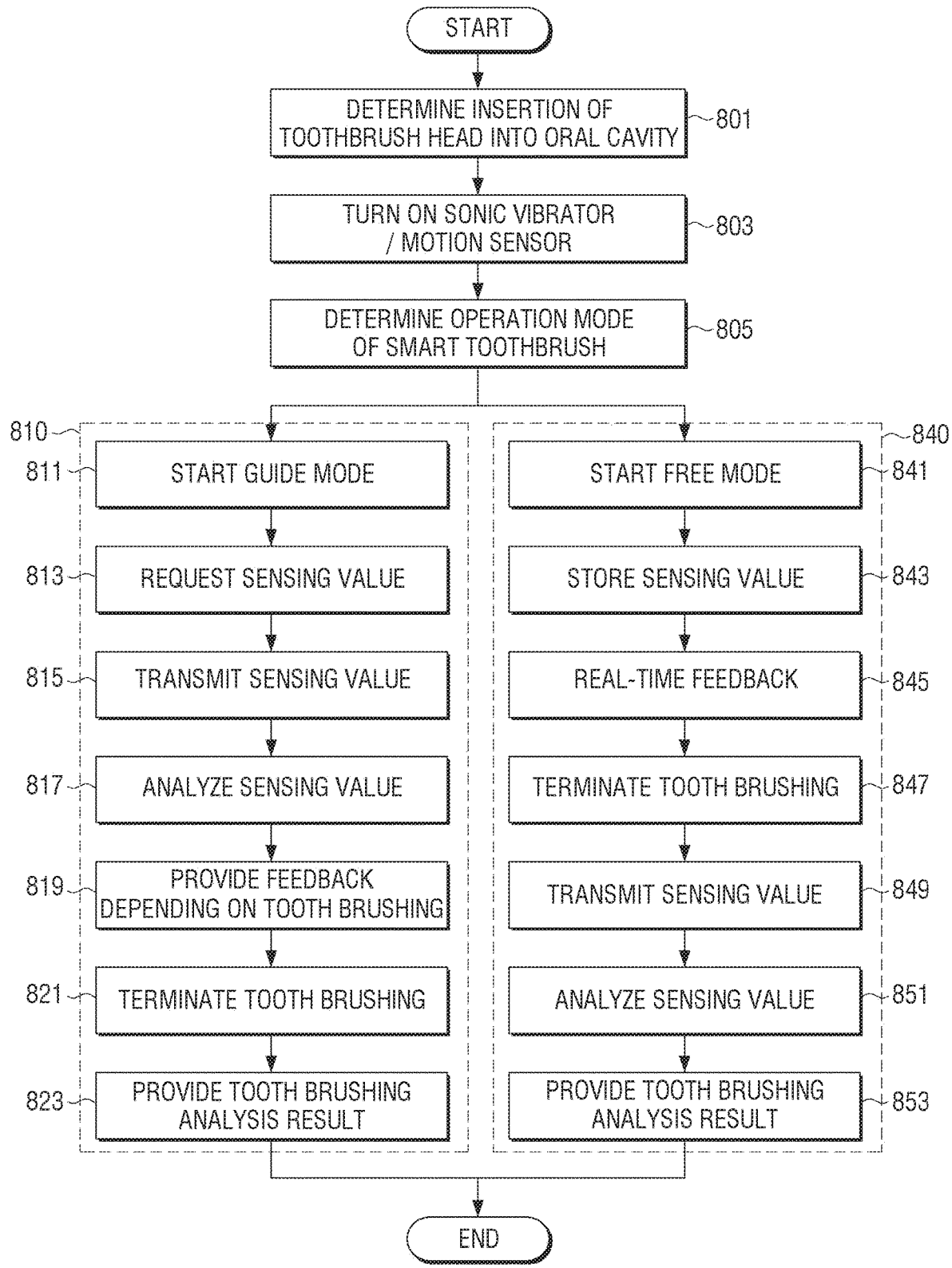
FIG. 8 is a flow chart illustrating operation modes of a smart toothbrush according to an embodiment of the present disclosure.

FIG. 8 is a flow chart illustrating operation modes of a smart toothbrush according to an embodiment of the present disclosure.

Referring to FIG. 8, in operation 801, as the user starts to brush teeth, the smart toothbrush may determine whether the head of the toothbrush is inserted into the oral cavity. A trigger signal informing the starting of the tooth brushing may be generated based on the change in the sensing value measured by the smart toothbrush. For example, the trigger signal may be generated based on the change in the temperature value of the temperature sensor on the handle of the smart toothbrush. For example, the trigger signal may be generated based on the change in the sensing value of the pressure sensor on the handle of the smart toothbrush.

Next, in operation 803, the smart toothbrush may turn on the sonic vibrator for generating a sound wave for tooth brushing. In addition, the smart toothbrush may turn on the motion sensor for the measurement of the sensing value.

In operation 805, the smart toothbrush may determine an operation mode of the smart toothbrush based on a position or a posture of the electronic device around the smart toothbrush.

For example, the smart toothbrush may determine an operation mode based on at least one of a relative distance between the electronic device therearound and the smart toothbrush and a mounting angle of the electronic device.

Specifically, if the distance between the smart toothbrush and the electronic device is within a certain distance (e.g., about 1 meter), and the mounting angle of the electronic device is positioned so that the screen of the electronic device and the smart toothbrush face each other, the smart toothbrush may be operated in the guide mode. Here, when a face of a user is recognized by a camera of the electronic device and the direction in which the screen of the electronic device is headed is horizontal or nearly horizontal with a ground, it may be determined that the screen of the electronic device and the smart toothbrush are positioned to face each other.

On the other hand, the information related to the position or posture of the electronic device may be determined by the electronic device and transmitted to the smart toothbrush. For example, the electronic device may determine the operation mode of the smart toothbrush to thereby transmit a triggering signal to operate the smart toothbrush.

On the other hand, if the smart toothbrush does not meet the guide mode conditions described above, the smart toothbrush may be operated in the free mode.

An operation 810 is an embodiment in which the smart toothbrush is operated in the guide mode, and an operation 840 is an embodiment in which the smart toothbrush is operated in the free mode.

In an embodiment, in operation 811, the smart toothbrush may start the guide mode.

In this case, in operation 813, the smart toothbrush may receive a request signal of the sensing value from the electronic device. For example, when a user executes an application (hereinafter, referred to as tooth brushing application) for guiding tooth brushing which is installed in the electronic device and performs a user input requesting the tooth brushing guide information, the electronic device may transmit a signal requesting the sensing value of the smart toothbrush.

In operation 815, the smart toothbrush may transmit the sensing values collected in the smart toothbrush to the electronic device in real time.

For example, the smart toothbrush may transmit the temperature value measured by the temperature sensor to the electronic device. Alternatively, the smart toothbrush may transmit the sensing value measured by the motion sensor to the electronic device. Alternatively, the smart toothbrush may transmit the bio-signal measured by the bio sensor to the electronic device.

In operation 817, the electronic device may analyze the received sensing values.

In operation 819, the electronic device may provide feedback information in accordance with the tooth brushing of the user. The feedback information may be the tooth brushing guide information for guiding the tooth brushing of the user, or the brushing analysis information of the user. The feedback information, for example, may be displayed on the screen of the electronic device, or may be provided as audio through the speaker of the electronic device. At this time, the tooth brushing analysis information may include, for example, the tooth brushing time per tooth brushing section, the tooth brushing area in which the user is brushing teeth, the brushing status information, and the like.

In operation 821, the tooth brushing of the user may end. As the user finishes tooth brushing, a signal informing the ending of the tooth brushing of the user may be transmitted from the smart toothbrush to the electronic device. Alternatively, the electronic device may determine that the tooth brushing ends based on analysis of the sensing value.

If the tooth brushing ends, in operation 823, the smart toothbrush may provide the tooth brushing analysis result. For example, the smart toothbrush may provide the tooth brushing analysis result based on the sensing values collected from the beginning to the end of the tooth brushing.

In another embodiment, in operation 841, the smart toothbrush may start the free mode.

In operation 843, the smart toothbrush may store the sensing values collected from the smart toothbrush. For example, the smart toothbrush may store the temperature value measured by the temperature sensor. Alternatively, the smart toothbrush may store the sensing value measured by the motion sensor. Alternatively, the smart toothbrush may store the bio-signal measured by the bio sensor.

In operation 845, the smart toothbrush may analyze the stored sensing values to provide feedback in real time.

For example, the smart toothbrush may analyze the sensing values to determine the tooth brushing time per tooth brushing section. The smart toothbrush may provide the tooth brushing guide information for guiding additional tooth brushing when the tooth brushing time per tooth brushing section is equal to or less than a threshold time. The tooth brushing guide information may include request information, time extension information, and the like, which induce teeth which are brushed insufficiently to be more brushed. Alternatively, the smart toothbrush may provide the tooth brushing analysis information. The smart toothbrush may provide the tooth brushing guide information or the tooth brushing analysis information visually, audibly or tactually. For example, the smart toothbrush may provide the information by voice. For example, the smart toothbrush may output voice saying "I need one more time to brush teeth". Alternatively, if the smart toothbrush is provided with a light emitter (for example, a light-emitting diode (LED) or the like), a flicker function of requesting additional tooth brushing by the light emitter may be performed.

In operation 847, the tooth brushing of the user may end.

In operation 849, if tooth brushing ends, the smart toothbrush may transmit the collected sensing values to the external electronic device. Alternatively, the smart toothbrush may transmit the tooth brushing guide information or the tooth brushing analysis information to the external electronic device.

In operation 851, the electronic device may analyze the received sensing values. Further, the electronic device can analyze the received tooth brushing guide information or tooth brushing analysis information.

In operation 853, the electronic device may provide the tooth brushing analysis result according to the analysis.

In addition, according to various embodiments of the present disclosure, the electronic device may display the tooth brushing guide information or the tooth brushing analysis information on the screen by naturally overlapping the tooth brushing guide information or the tooth brushing analysis information with the face of the user or the oral cavity of the user by the AR technique. Here, the AR technique may mean that a virtual image is displayed as a single image by being combined with a real world viewed by the user. The AR may also be called mixed reality (MR) because the real world is viewed as a single image by being combined with the virtual world having the additional information in real time.

In various embodiments, when the camera (e.g., a camera of an electronic device) is mounted in front of a user who is brushing teeth, the electronic device may display the tooth brushing guide information or the tooth brushing analysis information with an AR technique through the screen of the electronic device.

Specifically, the electronic device may compare the tooth brushing guide area which is the tooth brushing target area of the user displayed on the screen with the tooth brushing section in which the user is brushing teeth. The electronic device may display the feedback on the screen by the AR technique depending on how much the tooth brushing guide area and the tooth brushing section match each other.

For example, the electronic device may determine a tooth brushing score depending on the matching degree for each tooth brushing area within an oral cavity. If the tooth brushing score is equal to or less than a predetermined value, the electronic device may display the feedback inducing active tooth brushing on the screen.

Alternatively, the electronic device may generate feedback on the tooth brushing area in which a user is brushing teeth, tooth brushing time, a tooth brushing degree, a tooth brushing status as the tooth brushing analysis information and provide the feedback to the screen by the AR technique.

Alternatively, the electronic device may provide the feedback to the screen based on information (e.g., prescription information) on the oral cavity status history and oral cavity condition of the user by the AR technique.

Alternatively, the electronic device may provide feedback based on results (e.g., area in which cavities can be generated) obtained by analyzing the tooth brushing recording of the user to the screen by the AR technique. For example, the electronic device may provide a guide in consideration of the oral cavity status of the user. For example, a guide may be provided in consideration of the matters that some of the teeth of the user fall out or the number of teeth is many or few.

According to various embodiments, the electronic device may display the feedback on the bio information of the user determined based on the bio-signal measured by the bio sensor of the smart toothbrush on the screen by the AR technique. For example, the electronic device may provide different feedback effects by distinguishing between a case where the bio information of the user is within the normal range and a case where the bio information of the user is out of a normal range.

FIGS. 9A, 9B, 9C, 9D, 9E, and 9F are views illustrating screens to which the electronic device according to various embodiments of the present disclosure provide feedback information depending on the tooth brushing of the user.

Figures 9A, 9B:
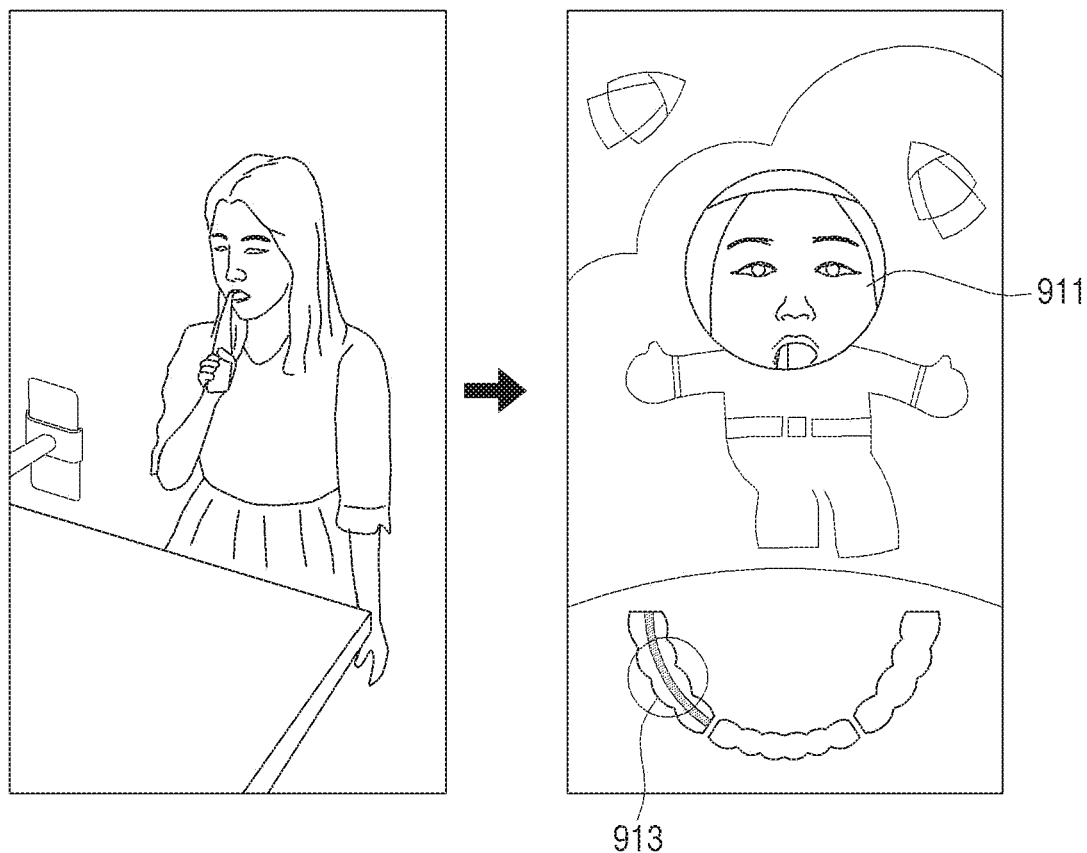
FIGS. 9A, 9B, 9C, 9D, 9E, and 9F are views illustrating screens providing feedback information depending on tooth brushing of a user according to various embodiments of the present disclosure.

Referring to FIGS. 9A, 9B, 9C, 9D, 9E, and 9F, first, as illustrated in FIG. 9A, a user of a smart toothbrush may start tooth brushing.

At this time, an external device facing the user may provide a tooth brushing application.

In order to trigger the tooth brush application execution, for example, when the user grasps the handle of the smart toothbrush or inserts the smart toothbrush into the oral cavity, the triggering signal may be transmitted to the electronic device. Alternatively, when the camera of the electronic device photographs that a user opens his/her mouth for tooth brushing or performs a gesture for tooth brushing, and the processor of the electronic device determines that the user starts tooth brushing based on the photographed image, the tooth brushing application may be executed based on the triggering signal generated according to the determination result. Alternatively, the user may search for the tooth brushing application and directly execute it.

Figures 9C, 9D:
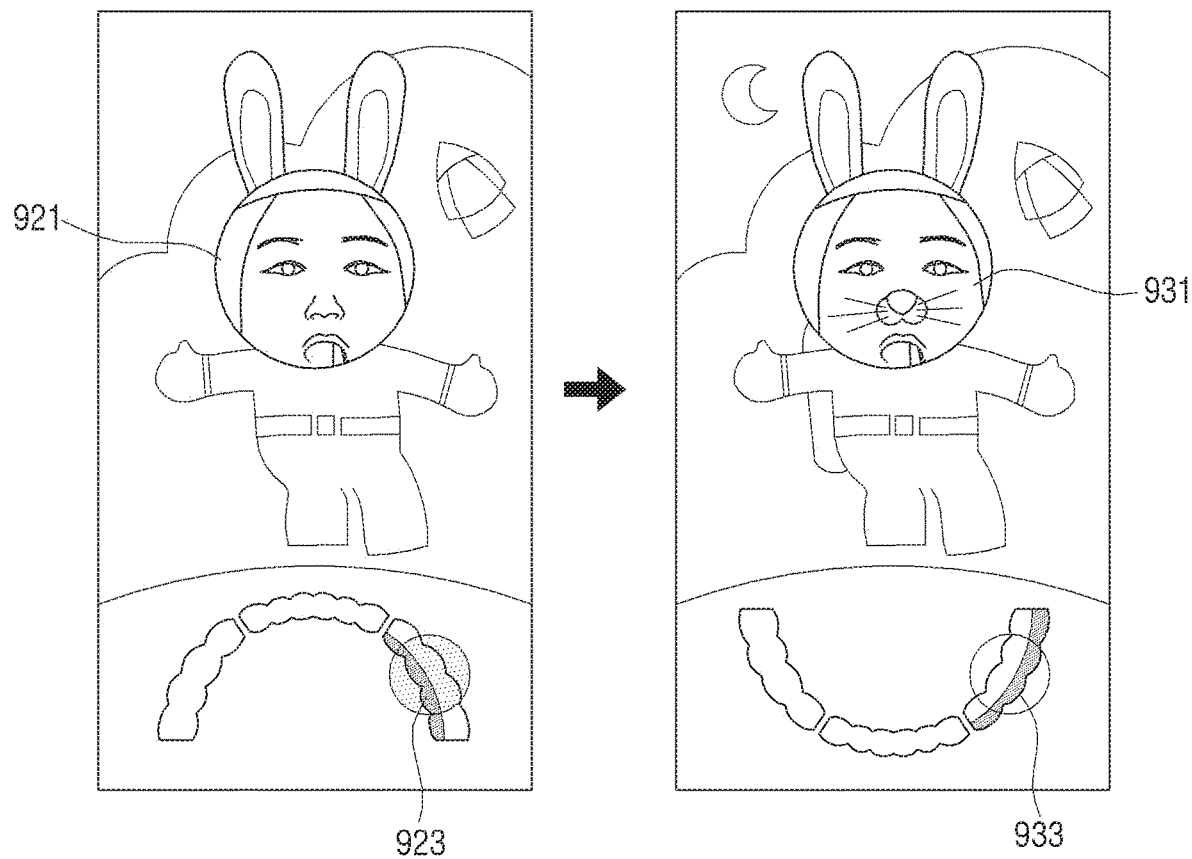

When the tooth brushing application is executed, the face or oral cavity of the user may be displayed on the screen of the electronic device by the AR technique as illustrated in FIGS. 9B, 9C, and 9D.

At this time, masks 911, 921, 931, and 941 may be displayed together with the face of the user. To this end, the electronic device may detect the face of the user from the user's photographing image. The masks may be displayed by overlapping the face of the user based on the detected singularities (e.g., eyes, nose, mouth, etc.) of the face. The masks 911, 921, 931, and 941 may be gradually changed to different forms as the tooth brushing of the user is performed.

In addition, the tooth brushing application may provide feedback by the AR technique, taking into account the tooth brushing area, the tooth brushing time and the tooth brushing status. At this time, various themes (for example, a jungle theme, a space theme, a school theme, etc.) may be displayed as a background together with the provision of the AR technique.

For example, when the tooth brushing guide area is divided into about 16 areas, the tooth brushing application may display the tooth brushing guide area, which sequentially guides 16 tooth brushing areas, on the screen while the user is brushing teeth.

The tooth brushing status may be displayed on the tooth brushing guide area in various colors according to the tooth brushing degree.

First, if the tooth brushing area in which the user is brushing teeth matches the tooth brushing guide area or if the matching rate between the tooth brushing area in which the user is brushing teeth and the touch brushing guide area is equal to or greater than (exceeds} a certain rate (for example, 80%), the tooth brushing application may represent tooth brushing guide areas 913 and 933 by a first color (for example, blue) as illustrated in FIGS. 9B and 9D in order to indicate that the user performs tooth brushing well according to the tooth brushing guide area.

Meanwhile, if the tooth brushing area in which the user is brushing teeth does not match the tooth brushing guide area or if the matching rate between the tooth brushing area in which the user is brushing teeth and the touch brushing guide area is less than (or equal to or less than) a certain rate (for example, 80%), the tooth brushing application may represent a tooth brushing guide area 923 by a second color (for example, red) as illustrated in FIG. 9C in order to indicate that the user does not perform tooth brushing well along the tooth brushing guide area.

In various embodiments, if the tooth brushing time of the user within the tooth brushing guide area is less than a certain time (for example, within 5 seconds to 10 seconds), the tooth brushing application may determine that the user does not perform tooth brushing well according to the tooth brushing guide area and represent the tooth brushing guide area by the second color.

In various embodiments, the tooth brushing application may instead display the tooth brushing status as an indicator at a location other than the tooth brushing guide area.

In various embodiments, if it is determined that tooth brushing has not been performed well according to the tooth brushing guide, the tooth brushing application may allocate more tooth brushing time to the tooth brushing area in which the tooth brushing is not performed well.

When the tooth brushing for the tooth brushing guide areas is completed, the tooth brushing application may allocate time to do gargle to a user. Even in this case, the tooth brushing guide information for guiding the user's gargle may be provided.

Figures 9E, 9F:
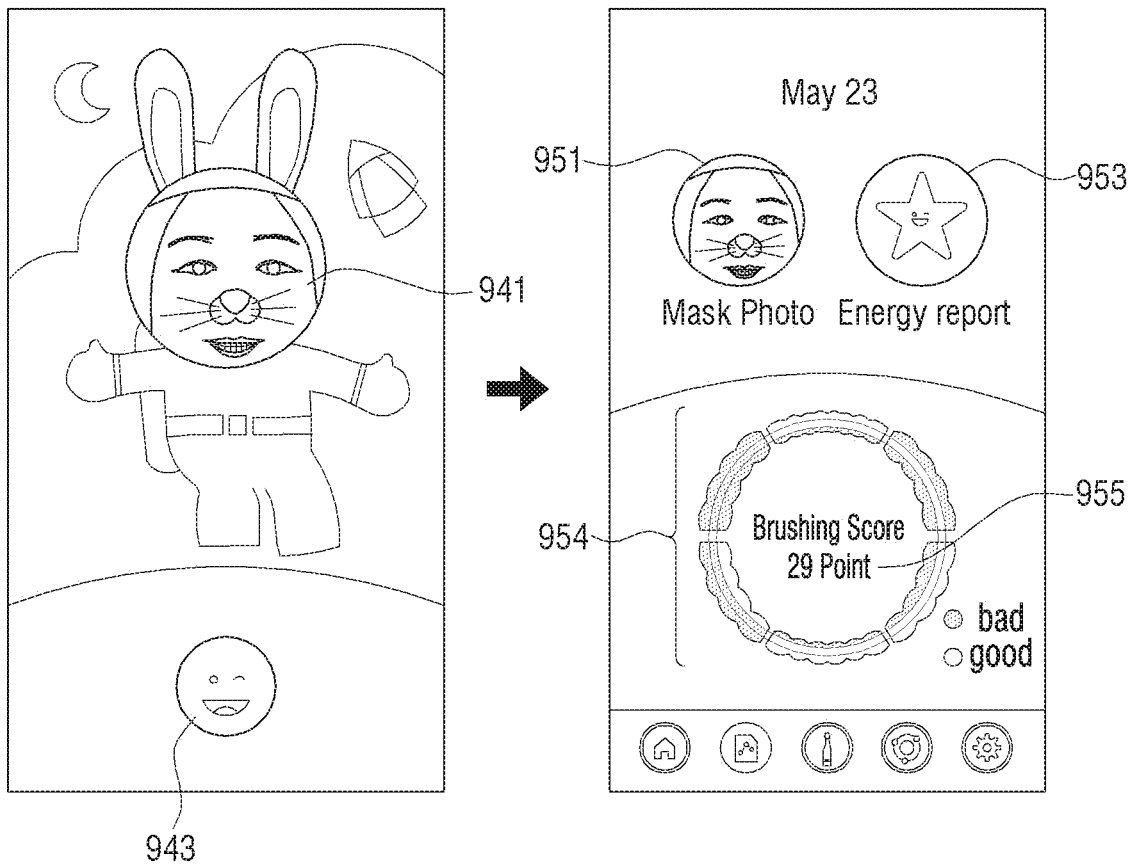

When the tooth brushing is completed, as illustrated in FIG. 9E, the electronic device may guide the user to take a picture. For example, a smiley emoticon 943 may be displayed or a sound 'smile' may be provided. Alternatively, the electronic device may automatically detect a smiling face of a user after the user has completed the gaggle. In this case, the electronic device may store as a photographed image an image at the time when the smiling face is detected.

When the photographing of the user is completed, as illustrated in FIG. 9F, the electronic device may provide a screen displaying the tooth brushing analysis result.

As the tooth brushing result, for example, a photograph 951 photographed in FIG. 9E, user's health condition information 953 based on the sensing value (e.g., temperature value) of the smart toothbrush, and entire tooth brushing status information 954 after the tooth brushing may be provided. According to various embodiments, a color of the mask on the oral cavity of the user as the indicator indicating the entire tooth brushing status may also be changed. For example, when the tooth brushing status is good, the color of the mask may be represented by the first color, and when the tooth brushing status is bad, the color of the mask may be represented by the second color.

Referring to FIG. 9F, the entire tooth brushing status information 954 after the tooth brushing may be shown for each tooth brushing area. For example, if a set of tooth surfaces is divided into 16 areas, the area in which the tooth brushing is performed well may be represented by a first color (for example, white), and the area in which the tooth brushing is not performed well may be represented by a second color (for example, yellow).

On the other hand, as illustrated by 955 in FIG. 9F, the entire tooth brushing status may be indicated by a score. For example, a score may be added to each of the sixteen areas, and a summed score or an average score of the sixteen areas may be displayed on the screen.

FIGS. 10A and 10B are screens illustrating history information according to various embodiments of the present disclosure.

As illustrated in FIG. 10A, the electronic device may show the tooth brushing history, and as illustrated in FIG. 10B, the electronic device may indicate the health condition of the user based on the bio-signal measured while a user is brushing teeth.

Referring to FIG. 10A, the tooth brushing history may be provided on a daily or weekly basis. Besides, it is needless to say that the tooth brushing history may be provided at various cycles such as 5 days, 10 days, month, year, and the like depending on the definition of the user.

In FIG. 10A, as an example, the tooth brushing history may be represented by a score. In this case, the score may be a score determined based on the whole tooth brushing status in FIG. 9D.

Referring to FIG. 10B, the health condition may be provided on a daily or weekly basis. Besides, it is needless to say that the health condition may be provided at various cycles such as 5 days, 10 days, month, year, and the like depending on the definition of the user.

The health condition of the user may be provided, for example, using a body temperature determined based on the temperature value within an oral cavity which is measured during the tooth brushing.

In this case, when the body temperature of the user is out of the appropriate range, it is determined that the health condition of the user is bad, and thus indicators 1001, 1002, 1003, and 1004 may be displayed at the corresponding temperature values.

As an example, the body temperature of the user may be related to melatonin hormone.

In this case, when the body temperature of the user is lowered, the secretion of the melatonin hormone is activated, and thus the health condition of the user may be determined to be bad.

On the other hand, when the body temperature of the user is increased, the secretion of melatonin hormone is suppressed, and thus the user's condition may be determined to be good.

According to the embodiment of the present disclosure, the smart toothbrush may measure a bio-signal in a non-restrained and non-conscious manner.

The non-restrained and non-conscious manner may mean, for example, naturally measuring the bio-signal of the user so that the user is not perceived.

The smart toothbrush may determine the bio information of the user using the smart toothbrush based on the measured bio-signal.

Alternatively, the smart toothbrush may transmit the measured bio-signal to the electronic device in communication with the smart toothbrush. In this case, the electronic device may determine the bio information of the user based on the received bio-signal.

The bio information of the user may be, for example, the body temperature, blood pressure, blood sugar, or body fat percentage of the user, and the bio-signal and the bio information may be the same value.

In an embodiment, when the smart toothbrush and the electronic device determine the body temperature of the user as the bio information, the user may determine whether the tooth brushing section in which the user is brushing teeth includes a body temperature measurement area associated with the measurement of the body temperature of the user.

If the smart toothbrush is located in the body temperature measurement area, the body temperature of the user may be determined based on the temperature value measured in the body temperature measurement area.

In various embodiments, the smart toothbrush may measure the temperature value in the body temperature measurement area by turning on a temperature sensor if it is determined that the tooth brushing section of the user is the body temperature measurement area. The body temperature of the user may be determined based on the measured temperature value.

Alternatively, the smart toothbrush may store temperature values per tooth brushing area and determine the body temperature of the user using the temperature measured in the body temperature measurement area among the stored temperature values.

Alternatively, the smart toothbrush may transmit the temperature value measured by the smart toothbrush to the electronic device. In this case, the smart toothbrush may transmit only the temperature value measured in the body temperature measurement area to the electronic device, or may transmit measured temperature values per tooth brushing area to the electronic device. The electronic device may determine the body temperature of the user based on the received temperature value. For example, when the measured temperatures per tooth brushing area are received, the electronic device may determine the body temperature of the user using the measured temperature in the body temperature measurement area among the tooth brushing areas.

Figures 11A, 11B:
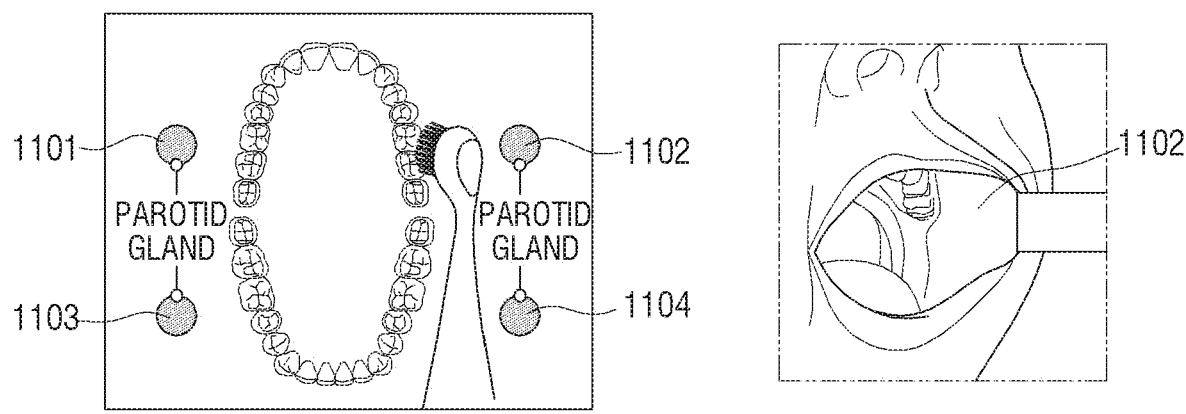
FIGS. 11A, 11B, and 11C are views illustrating processes of determining a body temperature of a user according to various embodiments of the present disclosure.
Figure 11C:
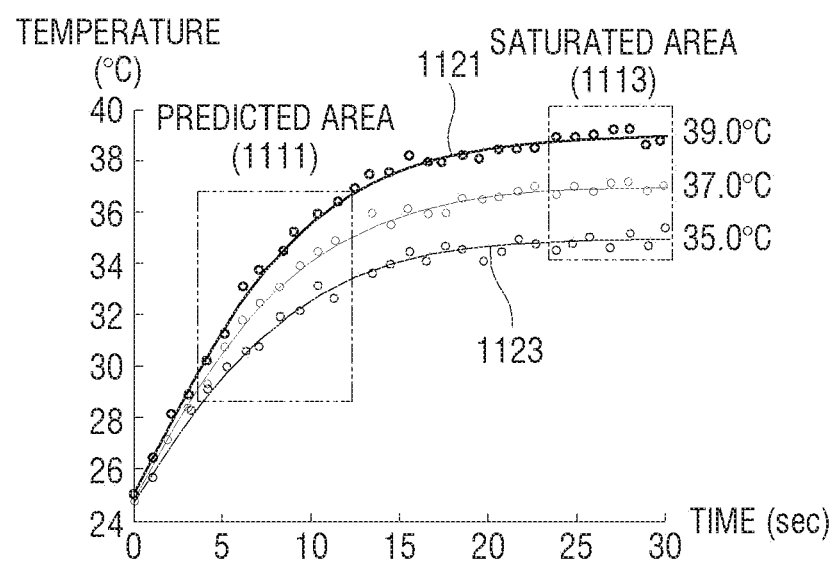

FIGS. 11A, 11B, and 11C are diagrams showing a process of determining a body temperature of a user.

Referring to FIGS. 11A, 11B, and 11C, first, during the tooth brushing of the user, the smart toothbrush may be located in parotid gland areas 1101, 1102, 1103, and 1104 while the user is brushing teeth.

In this case, the temperature sensor of the smart toothbrush may measure the temperature of the parotid gland area.

The smart toothbrush or the electronic device may determine the body temperature of the user based on the change rate of the measured temperature.

For example, FIG. 11C is a table showing the change in the body temperature of the user over time.

In the table of FIG. 11C, the change rate of the graph over time may be different according to the body temperature of the user.

For example, referring to a predicted area 1111 of FIG. 11C, as the body temperature of the user is increased, the change rate of the temperature of graph 1121 over time may be relatively large, and as the body temperature of the user is reduced, the change rate of the temperature of graph 1123 over time may be relatively low.

Therefore, if the change rate of the temperature of the predicted area is considered, it is possible to predict the body temperature of the user with the minimum time before the body temperature of the user reaches a saturated area 1113.

That is, it is possible to predict the body temperature of the user in a non-conscious manner while the user is brushing teeth.

For example, since an algorithm using a measured value in the saturated area 1113 is used in the case of using an oral thermometer which is placed at the sublingual gland, it takes about 2 to 5 minutes to measure the body temperature. In addition, since a separate oral thermometer is used, a user cannot but be aware of the process of measuring the body temperature.

On the other hand, when using an algorithm that uses the measured values in the predicted area 1111 according to the present disclosure, it may be possible to predict the body temperature of the user in a time of about 20 seconds to 30 seconds without the user's awareness.

Meanwhile, the electric toothbrush or the sonic toothbrush may be preferred to a scrubbing toothbrush as the smart toothbrush in order to ensure a time of about 20 seconds to 30 seconds for the body temperature measurement.

In this case, since no noise occurs due to the movement of the user's toothbrush, the body temperature may be measured more stably using the temperature sensor of the smart toothbrush.

According to various embodiments, it is possible to correct the temperature as much as the difference of the frictional heat in consideration of the frictional heat due to the motor vibration of the smart toothbrush in order to accurately determine the body temperature of the user.

In addition, the blood pressure of the user may be determined as the bio information based on the sensing value measured by the smart toothbrush.

Since a hand and a mouth corresponding to a contact point for blood pressure measurement are naturally secured by a tooth brushing operation of a user, electrocardiogram (ECG) measurement can be performed by sensors located on the toothbrush handle and the toothbrush head. In addition, it is also possible to measure a heart rate (PPG) by the sensor located on the handle of the smart toothbrush.

In this case, the smart toothbrush or the electronic device can calculate the blood pressure of the user based on the measured electrocardiogram and heart rate.

Particularly, if the smart toothbrush is the electric toothbrush or the sonic toothbrush, since an electrode sensor attached to the back surface of the toothbrush head is in contact with an inner area of a cheek of a user for a certain period of time, it is possible to more stably perform the heart rate measurement using the electrocardiogram sensor and the heart rate sensor.

Figure 12:
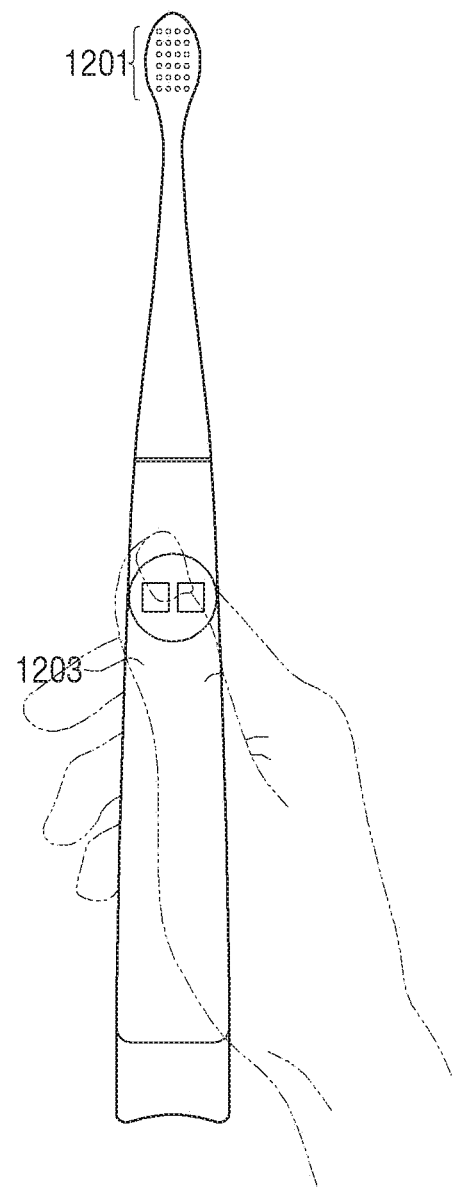
FIG. 12 is a view illustrating a smart toothbrush provided with an electrocardiogram sensor and a heart rate sensor according to an embodiment of the present disclosure.

FIG. 12 is a view illustrating a smart toothbrush provided with an electrocardiogram sensor and a heart rate sensor according to an embodiment of the present disclosure.

Referring to FIG. 12, an electrocardiogram sensor 1201 may be provided on the toothbrush head in an array type. At this time, the electrocardiogram measurement of the user may be performed by using stainless steel of the toothbrush head as a probe. In addition, the heart rate sensor may be positioned in an area 1203 with which a thumb of a hand of a user holding a toothbrush is in contact so as to be able to perform the measurement from the thumb, as in FIG. 12.

On the other hand, when the sonic toothbrush or the electric toothbrush is used, movement noise (e.g., rotation or ultrasonic waves) may occur due to a motor during the tooth brushing. In this case, since the movement noise has a repetitive pattern in a predetermined frequency domain, a process of eliminating the movement noise through a band pass filter may be added.

Further, according to various embodiments, the blood sugar of the user may be determined as the bio information based on the sensing value (for example, bio-signal) measured in the smart toothbrush.

For example, the user may perform tooth brushing to remove residues of food, and then position the bio sensor located on the toothbrush head in a salivary gland area (or a parotid duct area).

At this time, as a method of determining that the smart toothbrush is located in the saliva gland area, a method of determining a tooth brushing area using the above-mentioned motion sensor and temperature sensor may be used.

In this case, the smart toothbrush or the electronic device may calculate the blood sugar level of the user by measuring a concentration of sugar contained in saliva (for example, glucose) for a certain period of time (for example, about 10 seconds).

On the other hand, if food residue is left within the oral cavity of the user, a blood sugar value may be measured to be higher than an actual blood sugar value of the user due to the sugar in the food. Therefore, the time for measuring the blood sugar of the user may be limited to the time after the user removes food residue by gargle. Further, the time for measuring blood sugar of the user may be limited to the time after it is confirmed that the remnant of the salivary gland area has been removed.

In various embodiments, to confirm whether the food residue in the saliva gland area is removed, the smart toothbrush may measure blood sugar of the user by determining whether a user has enough performed tooth brushing in the tooth brushing guide area corresponding to the saliva gland area.

In addition, according to various embodiments, the body fat percentage of the user may be determined as the bio information based on the sensing value measured by the smart toothbrush.

For example, the smart toothbrush may introduce micro current into the body of a user through the toothbrush handle. The smart toothbrush may measure bio impedance, which is an electrical resistance measured by the sensor on the back surface of the toothbrush head.

Specifically, the smart toothbrush may use the bio impedance measured when the smart toothbrush is positioned in the buccal mucosa which is the inner mucosa of the cheek. At this time, as a method of determining whether the smart toothbrush is located in the buccal mucosa, a method of determining a tooth brushing area using the above-mentioned motion sensor and temperature sensor may be used.

If the bio impedance is measured, the smart toothbrush or the external device may calculate the body fat percentage of the user based on the measured bio impedance.

According to the embodiment of the present disclosure, the information (for example, sensing value, bio information, or the like) obtained by the smart toothbrush may be transmitted to the external server.

Alternatively, the tooth brushing analysis information of the user, the tooth brushing analysis result, the feedback information, the tooth brushing guide information, the health condition information or the like which is generated from the electronic device interlocked with the smart toothbrush may be transmitted to the external server.

The external server may analyze the user using at least one of the received information and may also transmit the received information or the analyzed information to the electronic device.

In addition, the smart toothbrush or the electronic device may receive necessary information from an external server during the tooth brushing, or transmit information generated during the tooth brushing to the external server in real time.

Meanwhile, the time or the period of requesting information to the external server or transmitting the information to the external server may be determined according to the result of the analysis of the sensing value measured. For example, if it is determined that the tooth brushing of the user starts based on the sensing value measured by the sensor of the smart toothbrush, the smart toothbrush or the electronic device may request information to the external server.

The server may analyze tooth brushing habits of a user based on the information related to the received tooth brushing. As the analysis result, a user group having a habit similar to the tooth brushing habits of the user may be searched, and feedback to guide the user to the correct tooth brushing habits may be transmitted to the smart toothbrush or the external device using the tooth brushing analysis result in the searched user group.

Alternatively, the server may interwork and analyze user's health information (e.g., eating habits, bowel records, sleep records, exercise records, medical records, etc.) related to the user which is being kept and the received information related to the tooth brushing to transmit the feedback guiding the correct tooth brushing habits to the smart toothbrush or the external device. As an example, the server may have a tooth prescription record (e.g., cavities decay or tooth extraction record) of a user. In this case, if the server receives a signal informing that the tooth brushing using the smart toothbrush is started from the electronic device or the smart toothbrush, the server may provide the tooth brushing guide information on the tooth brushing area according to the tooth prescription record to the electronic device or smart toothbrush. The tooth brushing guide information may include information such as, for example, extending the tooth brushing time of the area in which cavities are predicted or increasing the tooth brushing strength.

In various embodiments, the server may transmit the tooth brushing analysis result and the feedback guiding health condition, or health habits of the user to the electronic device of other users (e.g., a doctor or a parent) who are previously designated by the user. As a result, it is possible to continuously monitor and manage the tooth brushing habits of the user.

Figure 13:
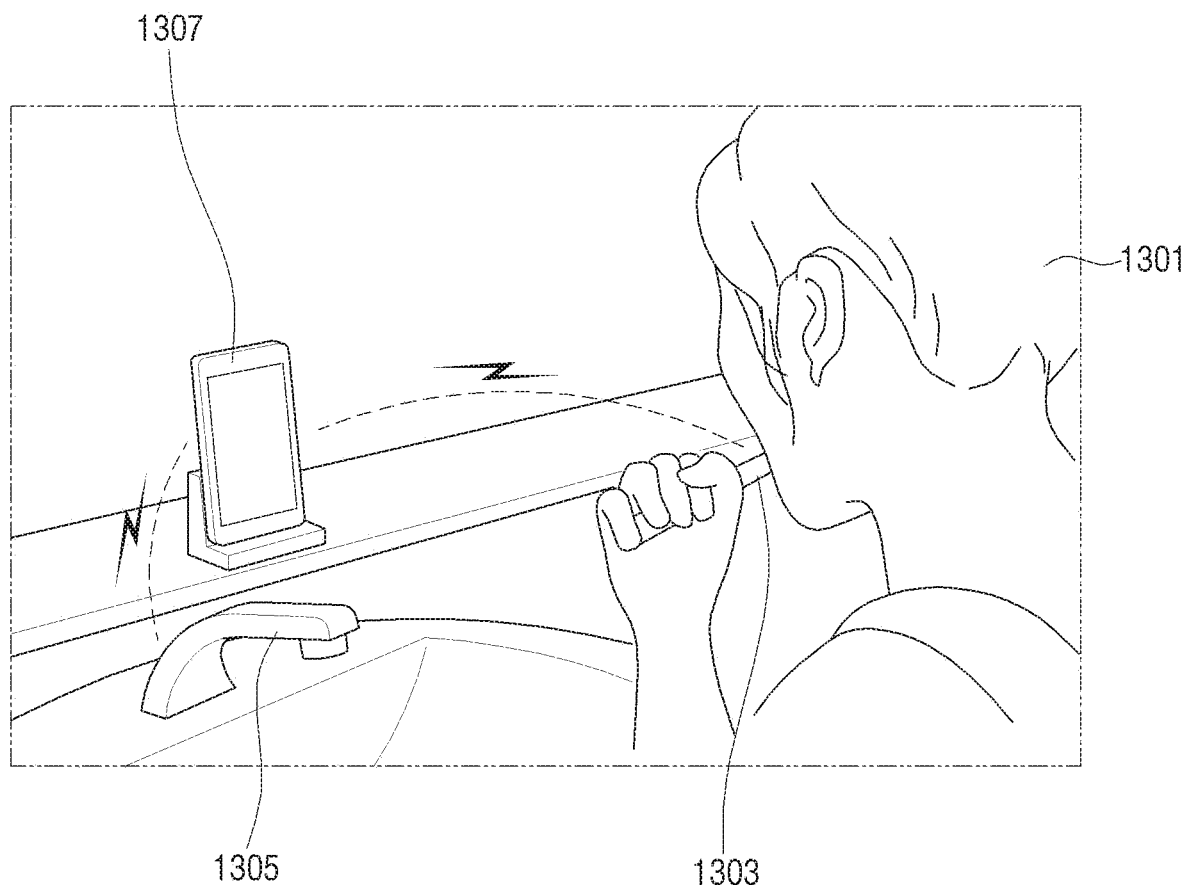
FIG. 13 is a view illustrating a situation in which a smart toothbrush is used in an Internet of things (IoT) environment according to an embodiment of the present disclosure.

FIG. 13 is a diagram illustrating the situation in which the smart toothbrush is used in an Internet of things (IoT) environment.

Referring to FIG. 13, the system of the IoT environment may include a sink for tooth brushing including an electronic device 1307, a smart toothbrush 1303 and an IoT device (e.g., faucet) 1305.

In the environment, if a user 1301 starts tooth brushing, the smart toothbrush 1303 or the electronic device 1307 may generate a triggering signal informing that the tooth brushing starts.

For example, if the user 1301 inserts the toothbrush into the oral cavity, the smart toothbrush 1303 may generate the triggering signal informing the start of the tooth brushing based on the rise in the temperature value measured by the temperature sensor of the toothbrush head. Alternatively, if the user 1301 holds the toothbrush, the smart toothbrush 1303 may generate the triggering signal informing the start of the tooth brushing based on the rise in the temperature value measured by the temperature sensor of the toothbrush handle. Alternatively, if the user 1301 pulls the smart toothbrush out of the charging pad, the charger of the smart toothbrush 1303 may generate the triggering signal informing the start of the tooth brushing based on the sensing value measured by a pressure sensor, a magnetic field sensor, a near range sensor, or the like of the charger. Alternatively, if the user 1301 performs a gesture to start the tooth brushing, the camera of the electronic device 1307 may generate the triggering signal informing the start of the tooth brushing based on the recognition result of the user's gesture.

The triggering signal generated from the smart toothbrush 1303 may be transmitted to the electronic device 1307. The electronic device 1307 may transmit the received triggering signal back to the IoT device 1305. In another embodiment, the triggering signal generated from the smart toothbrush 1303 may directly be transmitted to the IoT device 1305.

The IoT device 1305 may perform the operation of the IoT device 1305 based on the received triggering signal. For example, if the IoT device 1305 is a faucet, the faucet may provide an environment suitable for the tooth brushing of the user by opening the valve to allow inflow of water.

Figure 14:
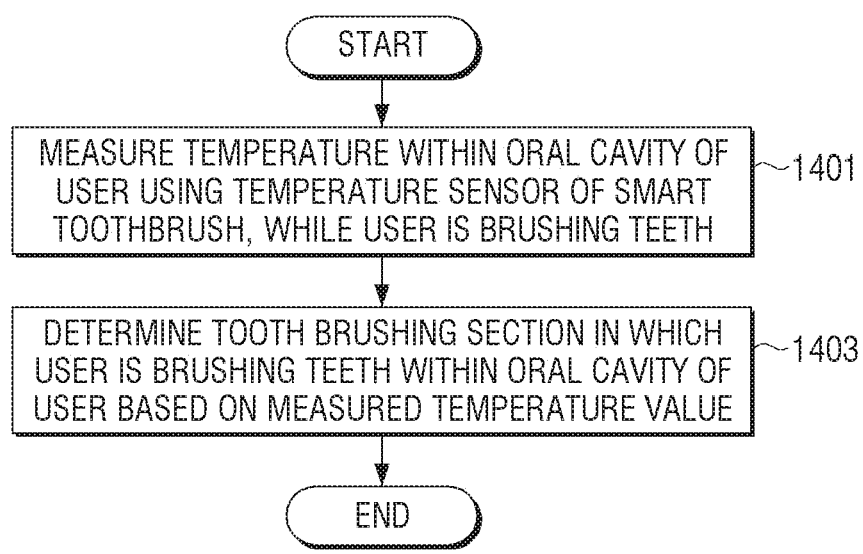
FIG. 14 is a flow chart illustrating processes in which a smart toothbrush determines a tooth brushing section according to an embodiment of the present disclosure.

FIG. 14 is a flow chart illustrating processes in which a smart toothbrush determines a tooth brushing section according to an embodiment of the present disclosure.

Referring to FIG. 14, first, in operation 1401, the temperature of the oral cavity of the user may be measured using the temperature sensor of the smart toothbrush while the user is brushing teeth.

Next, in operation 1403, the smart toothbrush may determine the tooth brushing section in which the user is brushing teeth within the oral cavity of the user, based on the measured temperature value.

In various embodiments, the smart toothbrush may also measure the movement of the smart toothbrush using the motion sensor of the smart toothbrush while the user is brushing teeth using the smart toothbrush. In this case, the smart toothbrush may determine the tooth brushing section in which the user is brushing teeth within the oral cavity of the user based on the measured temperature value and the measured sensing value.

In various embodiments, the smart toothbrush may transmit the measured temperature value to the electronic device in communication with the smart toothbrush. In this case, the electronic device may determine the tooth brushing section in which the user is brushing teeth within the oral cavity of the user based on the obtained temperature value.

In various embodiments, if the determined tooth brushing section includes the body temperature measurement area of the user, the smart toothbrush may determine the body temperature of the user based on the change rate of the temperature value measured in the body temperature measurement area. In this case, the smart toothbrush may transmit the determined body temperature value based on the change rate of the temperature value to the electronic device in communication with the smart toothbrush.

In various embodiments, the smart toothbrush may measure the tooth brushing time per tooth brushing section. If the tooth brushing time in the tooth brushing section is equal to or less than (or is less than) the threshold value or the tooth brushing time in the entire tooth brushing section is equal to or less than (or is less than) the threshold value, the tooth brushing guide information may be provided.

In various embodiments, the smart toothbrush may determine the operation mode of the smart toothbrush based on the position or posture of the electronic device around the smart toothbrush.

Figure 15:
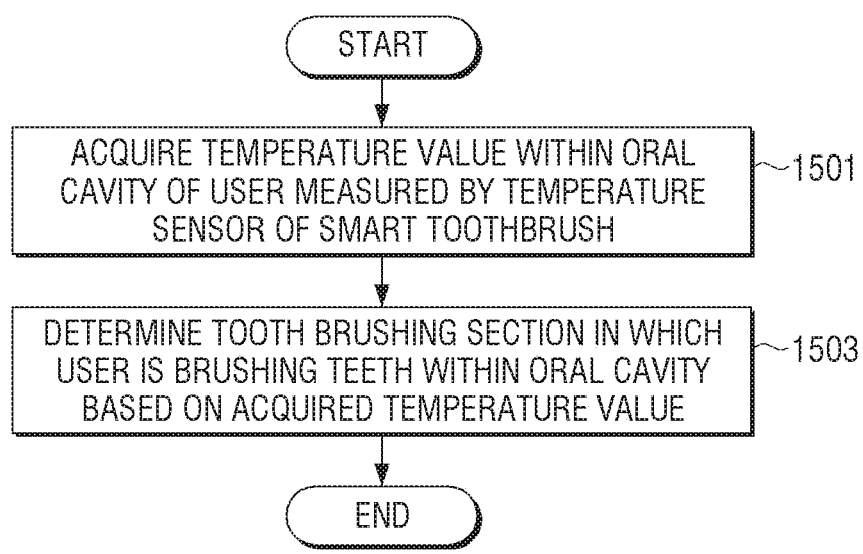
FIG. 15 is a flow chart illustrating processes in which an electronic device determines a tooth brushing section according to an embodiment of the present disclosure.

FIG. 15 is a flow chart illustrating processes in which an electronic device determines a tooth brushing section according to an embodiment of the present disclosure.

Referring to FIG. 15, first, in operation 1501, the electronic device may obtain the temperature value of the oral cavity of the user measured by the temperature sensor of the smart toothbrush while the user is brushing teeth.

Next, in operation 1503, the electronic device may determine the tooth brushing section in which the user is brushing teeth within the oral cavity of the user, based on the obtained temperature value.

In various embodiments, the electronic device may also obtain the measured sensing values using the motion sensor of the smart toothbrush while the user is brushing teeth. In this case, the electronic device may determine the tooth brushing section in which the user is brushing teeth within the oral cavity of the user based on the obtained temperature value and the obtained sensing value.

In various embodiments, the electronic device may display the tooth brushing guide information according to the comparison result of the tooth brushing section in which the user is brushing teeth and the tooth brushing guide area which is the tooth brushing target area of the user.

In various embodiments, the electronic device may display the tooth brushing guide information by the AR technique by overlapping the face of the user or the oral cavity of the user.

In various embodiments, the electronic device may display the tooth brushing analysis information that includes at least one of the tooth brushing time per tooth brushing section, the tooth brushing area in which the user is brushing teeth, and the tooth brushing status information.

Figure 16:
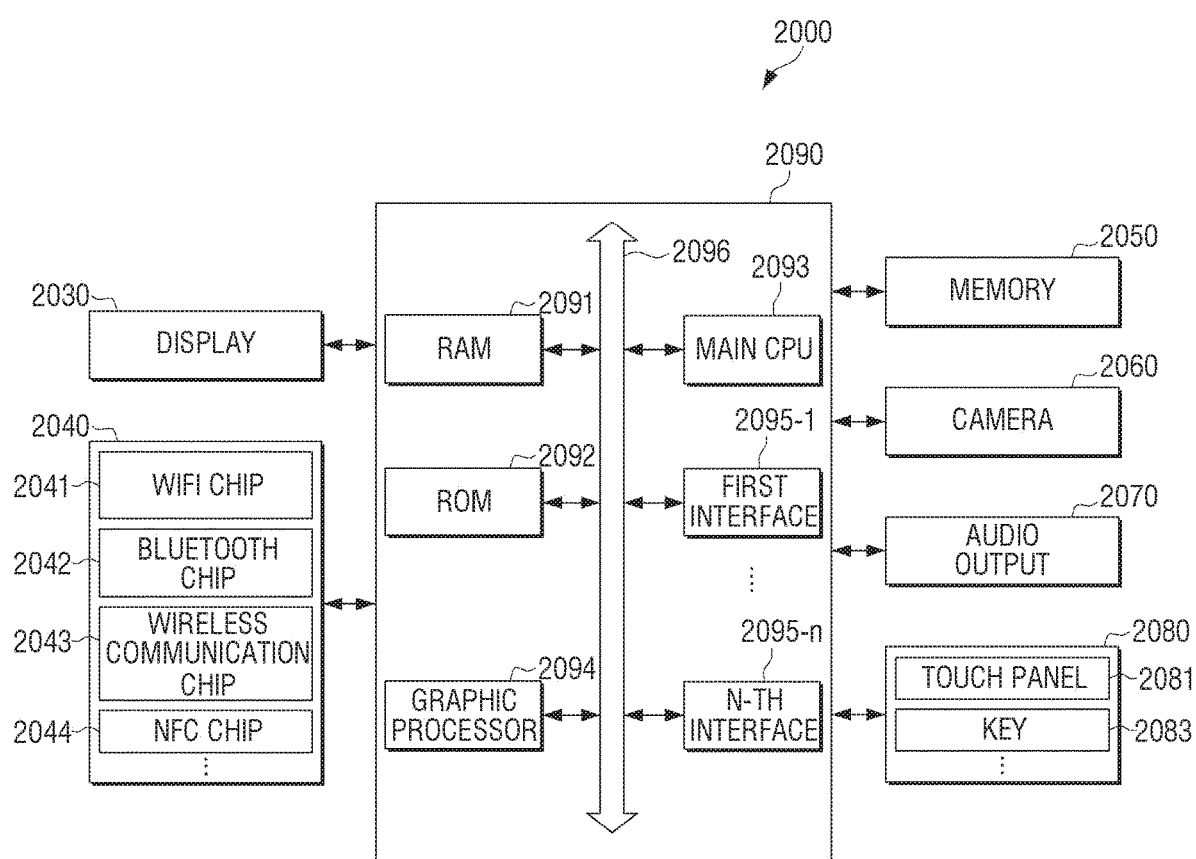
FIG. 16 is a block diagram illustrating an electronic device according to an embodiment of the present disclosure.

FIG. 16 is a block diagram illustrating the electronic device according to an embodiment of the present disclosure.

An electronic device 2000 of FIG. 16 may be an example of the electronic device 20 of FIGS. 1A to 1C. Alternatively, it may be an example of the electronic device of FIGS. 9A to 9F. Alternatively, it may be an example of the electronic device 1307 of FIG. 13.

Referring to FIG. 16, the electronic device 2000 may include at least one of a display 2030, a communication unit 2040, a memory 2050, a camera 2060, an audio output 2070, a user input 2080, and a processor 2090. On the other hand, the configuration of the electronic device 2000 illustrated in FIG. 16 is merely an example, and is not necessarily limited to the above-described block diagram. Therefore, it goes without saying that a part of the configuration of the electronic device 2000 illustrated in FIG. 16 may be omitted, modified or added depending on the kind of the electronic device 2000 or the purpose of the electronic device 2000.

The display 2030 may display visual information in a display area. The display 2030 may be coupled to at least one of a front region, a side region, and a rear region of the electronic device 2000 in the form of a flexible display. The flexible display may be warped, bent or wound without damage through a thin, and flexible substrate like paper.

The display 2030 may be combined with a touch panel to implement a touch screen having a layer structure. The touch screen not only has a display function but also has a function of detecting a touch input position and a touched area as well as a touch pressure and has a function of detecting not only a real-touch but also a proximity touch.

According to various embodiments, the display 2030 may display the tooth brushing guide information according to the comparison result of the tooth brushing section in which the user is brushing teeth and the tooth brushing guide area which is the tooth brushing target area of the user by using the smart toothbrush according to the present disclosure. In this case, the tooth brushing guide area may be changed according to at least one of the tooth brushing order, the tooth brushing time, and the oral cavity condition of the user.

Also, the display 2030 may display the tooth brushing guide information by the AR technique by overlapping the face of the user or the oral cavity of the user.

The communication unit 2040 may perform communication with various types of external devices according to various types of communication schemes. The communication unit 2040 may include at least one of a Wi-Fi chip 2041, a BT chip 2042, a wireless communication chip 2043, and an NFC chip 2044. The processor 2090 may use the communication unit 2040 to communicate with the smart toothbrush according to the present disclosure, the external server, or various external devices.

The memory 2050 may store various programs and data required to operate the electronic device 2000. The memory 2050 may be implemented as a non-volatile memory, a volatile memory, a flash memory, a hard disk drive (HDD), a solid state drive (SSD), etc. The memory 2050 is accessed by the processor 2090 and reading/recording/modification/deletion/update, etc., of data may be performed by the processor 2090. According to the present disclosure, the term memory 2050 may include a read-only memory (ROM) (not illustrated) and a random-access memory (RAM) (not illustrated) within the processor 2090 or a memory card (not illustrated) (for example, micro secure digital (SD) card, memory stick) equipped in the electronic device 2000.

Further, the memory 2050 may store programs, data, etc., for configuring various screens to be displayed in a display area of the display 2030.

The camera 2060 is, for example, a device that may photograph a still image and a moving image. According to an embodiment, the camera 2060 may include at least one image sensor (for example, front sensor or rear sensor), a lens, an image signal processor (ISP), or a flash. The camera 2060 may photograph a user who brushes teeth using the smart toothbrush according to the present disclosure.

The audio output 2070 may output various alarm sounds or voice messages in addition to various audio data. The audio output 240 may be implemented as a speaker, which is only an example. Therefore, the audio output 240 may be implemented as an output terminal through which audio data may be output.

The user input 2080 may receive various user inputs and transmit the various user inputs to the processor 2090. The user input 2080 may include, for example, a touch panel 2081 or a key 2083. The touch panel 2081 may use, for example, at least one of a capacitive type, a resistive type, an infrared type, and an ultrasonic type. Further, the touch panel 2081 may further include a control circuit. The touch panel 2081 may further include a tactile layer to provide a tactile reaction to a user. The key 2083 may include, for example, a physical button, an optical key, or a keypad.

The processor 2090 (or controller) may control the overall operation of the electronic device 2000 by using various programs stored in the memory 2050.

The processor 2090 may be configured to include a RAM 2091, a ROM 2092, a graphic processor 2094, a main CPU 2093, first to n-th interfaces 2095-1 to 2095-$n$, and a bus 2096. In this case, the RAM 2091, the ROM 2092, the graphic processor 2094, the main CPU 2093, the first to n-th interfaces 2095-1 to 2095-n, and the like may be connected to each other via the bus 2096.

The name of the components of the electronic device 2000 may be changed. Further, the electronic device 2000 according to various embodiments of the present disclosure may be configured to include at least one of the foregoing components and may not have some components or may further include other additional components.

According to various embodiments, the processor 2090 may use the smart toothbrush to obtain the temperature value within the oral cavity of the user measured by the temperature sensor of the smart toothbrush through the communication unit 2040 while the user is brushing teeth. The processor 2090 may determine the tooth brushing section in which the user is brushing teeth within the oral cavity of the user based on the obtained temperature value.

According to various embodiments, the processor 2090 may not only obtain the temperature value, but also obtain the sensing value measured by the motion sensor of the smart toothbrush while the user is brushing teeth through the communication unit 2040. The processor 2090 may determine the tooth brushing section in which the user is brushing teeth within the oral cavity of the user based on the obtained temperature value and the obtained sensing value.

The terms "~module" or "~unit" used in the present specification may mean a unit including one or at least two combinations of hardware, software, and firmware. The "module" may be interchangeably used with the terms unit, logic, logical block, part, circuit, or the like. The "module" may be a minimum unit of components integrally configured or some thereof. The "module" may also be a minimum unit performing one or more functions or some thereof. The "module" may be implemented mechanically or electronically. For example, the "module" may include at least one of an ASIC chip, FPGAs, or programmable logic device that performs some operations known or later developed.

According to various embodiments, at least some of devices (for example: modules or functions thereof) or methods (for example: operations) may be implemented as instructions stored in computer-readable storage media in, for example, a form of program modules. When the instructions are executed by the processor (for example: processor 13, processor 2090), the one or more processors may perform a function corresponding to the instructions. The computer-readable storage medium may be, for example, a memory (e.g., memory 14, memory 2050).

In addition, the program modules may be stored on a computer readable non-transitory recording medium and thus may be read and executed by a computer.

The non-transitory recording medium refers to a medium that semi-permanently stores data and is readable by a processor, as well as volatile or nonvolatile memory that temporarily stores data for operation or transmission, such as a register, cache, and buffer. On the other hand, intangible transmission media that may not be touched, such as signals, currents, etc., do not correspond to non-transitory recording media.

In detail, the program modules described above may be provided while being stored in the non-transitory computer readable recording medium such as a compact disc (CD), a DVD, a hard disk, a Blu-ray disk, a USB, an embedded memory of the electronic device according to the present disclosure, a memory card, a ROM, a RAM or the like.

In addition, the above-described program module may be stored in a memory of the server to be downloaded to the terminal (for example, the electronic device of the present disclosure) connected to the server by the network for sale, rental, subscription, or transfer. In this case, the program module described above may be uploaded to the server by a provider of the program (e.g., program developer, program manager, program tester, program modifier, or program manufacturer) for sale, rental, subscription, or transfer.

In addition, when the program module described above is provided from the server to the electronic device, at least a part of the program modules may be temporarily created in the buffer of the server for transmission. In this case, the buffer of the server may be the non-transitory recording medium of the present disclosure.

Further, when the above-mentioned programs are sold to an electronic device via a relay server (for example, a relay server in an area where the electronic device is located), at least a part of the programs may be temporarily stored in the buffer of the relay server. In this case, the buffer of the relay server may be the non-transitory recording medium of the present disclosure.

Further, the methods (e.g., operations) according to an embodiment of the present disclosure may be provided as a computer program product.

The computer program product may comprise the non-transitory recording medium on which the program modules described above are stored.

A computer program product may also refer to a product itself that may be stored as the non-transitory recording medium. In this case, the fact that the computer program product includes the non-transitory recording medium may mean that there is a situation in which the computer program product exists in the form of the non-transitory recording medium. That is, the computer program product may exist in the form of a medium that is uploaded or downloaded depending on the situation, or may exist in the form of the non-transitory recording medium. In this case, the product may be, for example, an application product itself sold in an electronic market (e.g., Android market, etc.).

According to various embodiments, the execution subject and the storage subject of the computer program product may be the same as or different from each other. For example, when the storage subject of the computer program product is a server, the execution subject of the computer program product may be a terminal (e.g., smart toothbrush, electronic device of the present disclosure).

According to various embodiments, there may be a system that includes both a computer program product and the smart toothbrush or the electronic device of which one function is performed by the computer program product. In this case, the electronic device may perform a function provided by the computer program product, under the control of another apparatus in which the computer program product is installed.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:
1. A smart toothbrush comprising:
   a toothbrush head configured to be provided with bristles;
   a toothbrush body configured to be connected to the toothbrush head and to be held;
   a temperature sensor configured to measure a temperature within an oral cavity of a user while the user is brushing teeth using the smart toothbrush; and a processor configured to:
  determine a tooth brushing section in which the user is brushing teeth within the oral cavity, based on a temperature value measured by the temperature sensor, and
  control intensity of vibration of the toothbrush head according to the determined tooth brushing section.

2. The smart toothbrush of claim 1, further comprising:
a motion sensor configured to measure a motion of the smart toothbrush,
wherein the processor is further configured to determine the tooth brushing section in which the user is brushing teeth within the oral cavity, based on the measured temperature value and a sensing value measured by the motion sensor.

3. The smart toothbrush of claim 1, wherein the tooth brushing section corresponds to at least one of tooth brushing areas that are divided into a tooth surface of the user, a set of a plurality of tooth surfaces, or spaces between teeth.

4. The smart toothbrush of claim 1, further comprising a communicator configured to transmit the measured temperature value to an electronic device that is in communication with the smart toothbrush.

5. The smart toothbrush of claim 1, wherein the processor is further configured to determine a body temperature of the user based on a rate of change in the temperature value measured in a body temperature measurement area when the determined tooth brushing section includes the body temperature measurement area associated with a body temperature measurement of the user.

6. The smart toothbrush of claim 5, further comprising a communicator configured to transmit a body temperature value determined based on the rate of change in the temperature value to an electronic device that is in communication with the smart toothbrush.

7. The smart toothbrush of claim 1, wherein the processor is further configured to measure a tooth brushing time per tooth brushing section and provide tooth brushing guide information, if the tooth brushing time is equal to or less than a threshold time.

8. The smart toothbrush of claim 1, wherein the processor is further configured to determine an operation mode of the smart toothbrush based on a position or a posture of an electronic device around the smart toothbrush.

9. The smart toothbrush of claim 1, wherein the toothbrush head and the toothbrush body have an integrated structure or a detachable structure in which the toothbrush head and the toothbrush body are separated from or coupled with each other.

10. The smart toothbrush of claim 1,
wherein the temperature sensor is provided on the toothbrush head, and
wherein the processor is provided on the toothbrush body.

11. An electronic device comprising:
a communicator configured to communicate with a smart toothbrush, the smart toothbrush including a toothbrush head; and
a processor configured to:
  acquire a temperature value within an oral cavity of a user measured by a temperature sensor of the smart toothbrush through the communicator,
  determine a tooth brushing section in which the user is brushing teeth within the oral cavity based on the acquired temperature value, while the user is brushing teeth using the smart toothbrush, and
  control intensity of vibration of the toothbrush head according to the determined tooth brushing section.

12. The electronic device of claim 11, wherein the processor is further configured to:
acquire a sensing value measured by a motion sensor of the smart toothbrush while the user is brushing teeth using the smart toothbrush through the communicator, and
determine the tooth brushing section in which the user is brushing teeth within the oral cavity, based on the acquired temperature value and the acquired sensing value.

13. The electronic device of claim 11, further comprising a display configured to display tooth brushing guide information according to the comparison result of the tooth brushing section in which the user is brushing teeth and a tooth brushing guide area which is a tooth brushing target area of the user.

14. The electronic device of claim 13, wherein the tooth brushing guide area is changed depending on at least one of a tooth brushing order, a tooth brushing time, or an oral cavity condition of the user.

15. The electronic device of claim 13, wherein the display is further configured to display tooth brushing guide information by an augmented reality (AR) technique by overlapping a face of the user or the oral cavity of the user.

16. The electronic device of claim 11, further comprising a display configured to display tooth brushing analysis information that includes at least one of tooth brushing time per tooth brushing section, a tooth brushing area in which the user is brushing teeth, or tooth brushing status information.

17. A method for determining a tooth brushing section of a smart toothbrush, the method comprising:
measuring a temperature within an oral cavity of a user using a temperature sensor of the smart toothbrush while the user is brushing teeth using the smart toothbrush, the smart toothbrush including a toothbrush head;
determining the tooth brushing section in which the user is brushing teeth within the oral cavity, based on the measured temperature value; and
controlling intensity of vibration of the toothbrush head according to the determined tooth brushing section.

18. The method of claim 17, further comprising:
measuring a motion of the smart toothbrush using a motion sensor of the smart toothbrush while the user is brushing teeth using the smart toothbrush,
wherein the determining of the tooth brushing section includes determining the tooth brushing section in which the user is brushing teeth within the oral cavity, based on the measured temperature value and a sensing value measured by the motion sensor.

* * * * *